(12) United States Patent
Egea et al.

(10) Patent No.: US 7,772,371 B2
(45) Date of Patent: Aug. 10, 2010

(54) STIMULATORS OF FACTOR X ACTIVATED (FXA) AS NEW TOPICAL ANTIHEMORRHAGIC AGENTS

(75) Inventors: Javier Pedreño Egea, Barcelona (ES); Luis Caveda Catasús, Miami, FL (US)

(73) Assignee: Thrombotargets Corporation, Miami, FL (US)

( * ) Notice: Subject to any disclaimer, the term of this patent is extended or adjusted under 35 U.S.C. 154(b) by 239 days.

(21) Appl. No.: 11/498,590

(22) Filed: Aug. 3, 2006

(65) Prior Publication Data

US 2007/0032424 A1 Feb. 8, 2007

Related U.S. Application Data

(60) Provisional application No. 60/719,643, filed on Sep. 21, 2005.

(30) Foreign Application Priority Data

Aug. 3, 2005  (EP)  ................................. 05380179

(51) Int. Cl.
*A61K 38/00* (2006.01)
*A61K 38/54* (2006.01)
*C07K 14/00* (2006.01)

(52) U.S. Cl. .................. 530/381; 424/78.02; 424/94.2; 514/2

(58) Field of Classification Search ........................ None
See application file for complete search history.

(56) References Cited

U.S. PATENT DOCUMENTS 4,721,618 A   1/1988  Giles et al.

| 5,017,556 A | * | 5/1991 | O'Brien et al. | 514/2 |
| 5,504,067 A | * | 4/1996 | Morrissey et al. | 514/8 |
| 6,036,955 A | * | 3/2000 | Thorpe et al. | 424/136.1 |

FOREIGN PATENT DOCUMENTS

| EP | 0266993 B1 | | 4/1995 |
| EP | 05380179.1 | * | 8/2005 |
| WO | 9402172 A1 | | 2/1994 |
| WO | 0004148 A1 | | 1/2000 |
| WO | 0230479 A1 | | 4/2002 |
| WO | 02086118 A1 | | 10/2002 |
| WO | 2006004675 A2 | | 1/2006 |

OTHER PUBLICATIONS

Hathcock et al., "Phospholipid regulates the activation of Factor X by Tissue Factor/Factor VIIa (TF/VIIa) via substrate and product interactions", Biochemistry 44: 8187-8197 (2005).*
Norledge, et al., "The Tissue Factor/Factor VIIa/Factor Xa Complex: A Model Built by Docking and Site-Directed Mutagenesis," Proteins: Structure, Function, and Genetics, vol. 53, (2003), pp. 640-648.
Carlsson, Karin, et al., Probing the interface between factor Xa and tissue factor in the quaternary complex tissue factor-factor VIIa-factor Xa-tissue factor pathway inhibitor, Eur. J. Biochem., 2003, pp. 2576-2582, vol. 270.

* cited by examiner

*Primary Examiner*—Anand U Desai
(74) *Attorney, Agent, or Firm*—Tristan A. Fuierer; Moore & Van Allen, PLLC

(57) ABSTRACT

The activated coagulation Factor X (FXa) stimulating agents may be used in the treatment of hemorrhages in a subject. Compounds and combinations are described which are particularly useful for the topical treatment of hemorrhaging in healthy subjects or in patients with hemorrhagic diathesis.

17 Claims, 3 Drawing Sheets

* DIC: Disseminated Intravascular Coagulation

STIMULATORS OF FACTOR X ACTIVATED (FXA) AS NEW TOPICAL ANTIHEMORRHAGIC AGENTS

CROSS REFERENCE TO RELATED APPLICATIONS

This application claims priority under 35 U.S.C. §119(a) of European Patent Application No. 05380179.1 for "Activated Factor X Stimulants as New Antihemorrhagic Agents for Topical Use," filed on Aug. 3, 2005 in the name of Javier Pedreño Egea et al., and under 35 U.S.C. §119(e) of U.S. Provisional Patent Application No. 60/719,643 for "Activated Factor X Stimulants as New Antihemorrhagic Agents for Topical Use," filed on Sep. 21, 2005 in the name of Javier Pedreño Egea et al., both of which are incorporated by reference herein in their entirety.

FIELD OF THE INVENTION

This invention relates to the topical treatment of hemorrhages in a subject by means of the use of FXa stimulators. This invention is based in the discovery that lipidated Tissue Factor (TF) exerts a new regulatory role stimulating all proteolytic activities (amidolytic and prothrombin hydrolytic activity) of both forms of FXa, soluble and bound to prothrombinase complex.

BACKGROUND OF THE INVENTION

1. Physiology of Coagulation

Hemostasis is the mechanism by means of which living beings respond to a hemorrhage and involves the participation of two processes that become functional immediately after a lesion and remain active for a long period of time. The first of them is known as primary hemostasis and is characterized by the occurrence of vasoconstriction at the vascular lesion site and platelet aggregate formation. The second one is known as secondary hemostasis, being the phase in which the fibrin clot is formed due to the action of the different coagulation cascade proteolytic enzymes.

Platelet aggregate plays a key role in hemostasis in capillaries, being particularly relevant in mucocutaneous hemorrhages. In contrast, fibrin clot formation is much more important in large vessel hemostasis, being more relevant in internal hemorrhages (gastrointestinal, cerebral, etc.). The following phases can be distinguished during platelet aggregate formation: (i) platelet adhesion to the sub-endothelium surface exposed by the lesion; (ii) release of the granular content of platelets as a response to their activation; (iii) platelet aggregation with the subsequent sequestering and concentration of more platelets at the lesion site; and (iv) binding of fibrinogen as well as other coagulation proteins to the platelet surface to produce thrombin and form the fibrin clot that will allow the plates to become fused and consolidated, thus stabilizing the hemostasic clot. Furthermore, it is well known that platelet count is critical for fibrin clot formation; platelet counts below 20,000 per µl are accompanied with severe bleeding episodes.

Several cofactors and proteolytic enzymes participate in the second phase of the blood coagulation process, all referred to as coagulation factors, and it consists of several phases ending with fibrin formation from fibrinogen hydrolysis due to the action of thrombin. Furthermore the thrombin production enhances the platelet aggregate by increasing the activation and aggregation of more platelets. Thrombin is previously formed by proteolytic hydrolysis of an apoenzyme, prothrombin. This proteolysis is carried out by the serine protease FXa, which binds to the surface of the activated platelets and only in the presence of its cofactor, activated coagulation factor V (FVa), and calcium ions, this serine protease is able to hydrolyze prothrombin. FXa can occur by two separate pathways, the intrinsic pathway and the extrinsic pathway.

The intrinsic pathway consists of a series of reactions involving mainly coagulation factor VIII (FVIII), coagulation factor IX (FIX) and coagulation factor XI (FXI), in which each proenzyme is hydrolyzed, yielding its active protease form (FVIIIa, FIXa and FXIa). In each step, the recently formed proteolytic enzyme will catalyze activation of the following proenzyme to successively yield the active form. Activation of the different coagulation factors involved in the intrinsic pathway takes place; therefore, in the manner of a cascade, a deficiency of any of the proteins of the intrinsic pathway blocks activation of the following step, preventing clot formation and increasing hemorrhagic tendency. Deficiencies of different coagulation factors, for example, FVIII, FIX or FXI, cause severe hemorrhagic syndromes, such as hemophilia A, B and C, respectively.

In the blood coagulation extrinsic pathway, the TF exposed on adventitia cells at the lesion site, binds to circulating coagulation factor VII/activated coagulation factor VII (FVII/FVIIa) to form the TF::FVIIa complex and, in the presence of calcium, to act as a substrate for FX activation. The extrinsic pathway is currently considered the most relevant pathway in blood coagulation, and it is accepted that in the event of a hemorrhage produced by a vascular lesion, coagulation is triggered due to extrinsic pathway activation involving the interaction of TF with its ligand, FVII/FVIIa.

Another role assigned to the TF::FVIIa complex in coagulation is to act as a substrate so that FX activation takes place due to FVIIa As a result, basal FXa levels (<150 pM), which initially are insufficient to generate fibrin clot formation, increase. This increases in basal FXa concentrations in the presence of its cofactor, FVa, and of a cellular procoagulant surface, would be able to produce the thrombin required for fibrin clot formation. It is currently accepted that once the platelets are activated, they play a key role in blood coagulation. They provide the procoagulant surface rich in anionic phospholipids and on the other hand they expose the FVa and FXa factors stored within them. All this allows correct assembly of the different agents involved in coagulation on the surface of their plasma membranes forming the well known prothrombinase complex (which includes FXa, FVa, prothrombin, and an anionic procoagulant platelet phospholipid surface).

The theory of extrinsic pathway activation is capable to explain how coagulation begins through the role that has been attributed to the TF::FVIIa complex. One example illustrating the biological relevance of the TF::FVIIa complex in the blood coagulation process is the Disseminated Intravascular Coagulation (DIC) Syndrome. This clinical condition is associated with the intravascular release of TF and can occur in the course of severe clinical conditions (shock, sepsis, cardiac arrest, major trauma, liver disease, major surgery, burns, etc).

Evidently in a context in which FVIIa is not present, as occurs in a congenital deficiency of this factor, coagulation hypothetically will never take place since FX will not be activated at sufficient levels and, consequently, hemorrhagic manifestations should be fatal. Murine models confirm this theory and FVII deficiency is incompatible with life, being accompanied by severe fatal hemorrhages. However, congenital FVII deficiencies described in humans until now, are not always accompanied by hemorrhages. Cases of complete FVII deficiency with no clinical symptoms and occurring in healthy individuals with no hemorrhagic complications have been reported. All this suggests that other trigger coagulation mechanisms independent of FVII must exist in humans.

TF is an integral membrane glycoprotein belonging to the super-family of class II cytokine receptors specifically binding to FVI/FVIIa and plays a relevant role in the blood coagulation extrinsic pathway. The physiological roles assigned to TF are well known; on one hand, it is a receptor specific for FVIIa and, once the TF::FVIIa complex has been formed, it acts as a substrate so that FX activation takes place. In fact, after a vascular lesion, TF, which is normally sequestered on the surface of adventitia cells externally surrounding blood vessels, comes into contact and interacts with its ligand, FVII present in blood, to form the TF::FVII complex. Once this complex is formed, FVII autoactivation takes place, yielding its active form FVIIa. There is currently extensive information on the TF::FVII complex structure. The main FVII binding sites participating in the interaction with TF are located in the first domain similar to that of the epidermal growth factor (EGF) and in the protease domain. On the other hand, it has also been reported that other less relevant binding sites participate (4-carboxyglutamate-rich domain (Gla domain) and the second EGF domain). The binding sites present in TF are located in the two type III fibronectin domains and in the intermediate region between both domains.

Recent studies have allowed identifying that TF Lysine 165 and Lysine 166 residues interact with the Gla domain of FX, both in the activated and non-activated forms. However, in contrast with that which occurs with information referring to the TF::FVIIa complex little is known about the interaction of TF with FX and FXa. First, data suggests that Lys (165 and 166) residues act as a substrate for FX activation. On the other hand, it has been recently described that TF can acts as FXa cofactor for FVII activation. That is, the binding of FVII to TF stimulates FVIIa autoactivation and FX activation. After, FXa bound to TF stimulates FVII activation which, in turn, will increase FX activation, and consequently proturombin hydrolysis and fibrin clot formation.

The inventors have discovered that the postulated role of TF as cofactor for FXa is much more relevant becoming critical for hemostasis. Despite to the accepted role of TF as membrane receptor for FVII, the inventors have shown that TF is also a potent FXa stimulator. TF acts as stimulator of FXa producing a significant enhance in its proteolytic activity. "Stimulators of FXa" as used in this description makes reference to all forms of FXa, such as FXa soluble and FXa bound to prothrombinase complex.

It is well known that FXa at picomolar concentrations is unable to produce any effect on coagulation, even in the presence of its well known cofactor, FVa (see table 9). Therefore, under these conditions prothrombinase complex is not active. Surprisingly, in the presence of TF (i.e. injury or exogenous administration), FXa at picomolar concentrations (i.e. physiological basal concentrations or exogenously administered) cause prothrombin hydrolysis, leading to fibrin clot formation, even in the absence of FVII/FVIIa (table 7).

In the present patent application the inventors describe that TF::FXa interaction is a new trigger coagulation mechanism independent of the TF::FVIIa complexes and the extrinsic coagulation pathway.

Finally, it is well known that there are certain platelet diseases occurring with disorders in platelet aggregation and a greater tendency of hemorrhagic episodes, amongst which Glanzmann's disease and the Bernard-Soulier Syndrome stand out, in which congenital defects affecting the fibrinogen receptor or the Gp1b receptor, respectively, have been disclosed. On the other hand, severe hemorrhagic episodes are present in congenital and acquired thrombocytopenic disorders when platelet count decreases below 20,000 per µl.

In the present patent application, the inventors have demonstrated that lipidated TF is also effective in the treatment of hemorrhages present in congenital, acquired platelet diseases and severe Thrombocytopenic disorders (below 9,000 per µl).

2. Coagulation Pathology

Congenital deficiencies of each coagulation factor can be associated with the occurrence of hemorrhages and generally involve a single protein; thus, for example, hemophilia A is a hereditary hemorrhagic disease affecting FVIII. Acquired coagulation diseases occur in individuals with no prior history of bleeding and may have multiple sources; by way of illustration, the presence of inhibitors specific for coagulation factors may occur in individuals who have been subjected to many transfusions. Although acquired coagulation factor deficiencies are an unknown etiological entity also causing severe hemostasic problems, they are also one of the most important problems in multiple transfusions to which patients with congenital coagulopathies are subjected. Other important source of acquired coagulation disorders are anticoagulant therapies, such as heparin and warfarin drugs. A significant percentage (5-10%) of patients treated with anticoagulant drugs present bleeding episodes most of them are difficult to manage.

As it has been previously mentioned, congenital and acquired platelet disorders can be also associated with hemorrhages. Platelet count decreases (below 20.000 per µl) may cause fibrin clot impairment frequently accompanied with severe bleeding episodes.

The currently available therapeutic arsenal in a mild/moderate or severe/fatal hemorrhage (by surgery or external trauma) is very limited. There are different hemostatic agents that are able to accelerate blood coagulation and preventing hemorrhages, for example (1) human-derived blood products, such as coagulation factor concentrates and local hemostatic agents, such as fibrillar collagen, fibrin glue and prothombin complex concentrates; (2) human recombinant proteins; (3) antifibrinolytics drugs, such as aminocaproic acid, tranexamic acid; and (4) inorganic local hemostatic agents, such as silica and caolin surfaces.

The following critical limitations have been reported:
  (1) Intravenous administration
  (2) Special device requirement for administration
  (3) Narrow therapeutic focus
  (4) Inappropriate or troublesome treatment to be administrated in specific bleeding episodes
  (5) Lack of acute effect
  (6) Instability of fibrin clot
  (7) Very dangerous side-effects
  (8) Expensive treatment Human Derived Blood Products (Coagulation Factor and Platelet Concentrates)

It is a high expensive and low available treatment that it must always be intravenously administered. It has a very narrow therapeutic focus, it is only useful to treat their specific deficiency. It is inappropriate to topically treat any kind of bleeding episodes. It is not useful to acutely treat an hemorrhage because it requires long administration protocols to be effective, and above all is a very dangerous treatment: 20% of hemophilic patients have developed hepatitis, 5% HIV, and up to 15% present plasmatic antibodies against FVIII or FIX (acquired hemophilia) that requires special and very expensive substitutive treatments (immunosuppressant, high doses of coagulation factors, plasmapheresis, etc). For these reasons, public health organizations (WHO, FDA, EMEA, etc) are very interested in the development of new hemostatic agents better than coagulation factor concentrates.

Local Hemostatic Agents

It is an expensive treatment inappropriate to be administrated in some bleeding episodes (i.e. epistaxis), troublesome for dental treatment, form unstable fibrin clot, and as coagulation factor concentrates have the same potential dangerous side-effects. They should not be used in patients who have never received human-derived blood products or those who are receiving treatment with recombinant FVIII or FIX because of the potential risks of human viral transmission.

Human Recombinant Proteins

It is the most expensive treatment (average cost of 6,000 €) only available for developed countries. As coagulation factor concentrates, it must always be intravenously administered, has a very narrow therapeutic focus because it is only useful to treat their specific deficiency, is inappropriate to topically treat hemorrhages, is not useful to acutely treat an hemorrhage because it also requires long administration protocols to be effective, and although no human viral transmission has been reported, the same percentage of acquired hemophilia has been described (up to 15% present antibodies anti FVIII or FIX). As coagulation factor concentrates, public authorities greatly limit its use.

Antifibrinolytic Drugs

They have a narrow therapeutic focus this being its most relevant limitation. These drugs require previous fibrin clot formation to be effective. Therefore, they are only useful in healthy subjects, however when fibrin clot is inappropriately formed (i.e. congenital coagulopathies, such as hemophilia, FVII deficiency) their therapeutic efficacy dramatically decreases. Moreover, they are not useful to acutely treat a hemorrhage because they also require long administration protocols to be effective.

Inorganic Local Hemostatic Agents

The most important restriction for the use of these hemostatic agents is that they are inappropriate to be administrated in much kind of hemorrhages, such as epistaxis, dental, and surgical. Moreover, a painful exothermic reaction has been reported, reducing significantly its use only for mucocutaneous bleeding in critical situations (wars).

In conclusion, surprisingly there are no drugs available today useful for the topical treatment of a simple episode of epistaxis or gingival dental bleeding after brushing one's teeth or simply due to an everyday wound caused by shaving, due to the punctured vein in a blood extraction, or due to the wound from an accidental fall in the street. The problem is further aggravated in the case of patients with hemorrhagic diathesis, for example with congenital coagulopathies of the hemophilia type or the von Willebrand disease or patients with congenital platelet disorders, of the Glanzmann's disease type or the Bernard-Soulier syndrome, or acquired coagulopathies. These patients have serious problems with day to day living and in a simple dental extraction or in any minor trauma causing a bleeding wound they have no medical treatment available to improve their quality of life. The problem obviously becomes greater when these patients suffer an external trauma or severe bleeding accident since their life is at serious risk. In all these situations, the only available pharmacological tool is the administration of human plasma containing the deficient factors or the human recombinant factor specific for each coagulation factor. All these therapies imply using the parenteral route and, therefore, are not designed to be used with great frequency, as would be the case, for example, in any daily mild or moderate bleeding. Finally, it is widely accepted that new local hemostatic agents without the limitations previously described, will represent a significant improve of present treatment which will reduce both the cost and the high prevalence of side-effects.

3. Background of the Invention

Until now it has been accepted that TF is the main element responsible to trigger blood coagulation. For coagulation to begin, it is absolutely necessary activation of FX to FXa to start prothrombin hydrolysis. The source of this FXa has mainly been attributed to the interaction of FVIIa with its receptor, TF. Although it has been described that FXa is present in platelet granules and that it may be exposed on the surface when its activation takes place, the physiological concentrations of FXa (<150 pM) present in blood are insufficient to begin thrombin formation, even in the presence of its cofactor, FVa and of a platelet procoagulant surface (FIG. 1). Therefore, it is currently accepted that coagulation can only start when FXa basal concentrations significantly increase. The source of the increase of FXa basal concentrations has always been attributed to both, the TF::FVIIa complex and FIXa proteolytic activities (FIG. 2).

Lipidated TF recombinant proteins have been able to accelerate only in vitro conditions, coagulation in both healthy and hemophilic blood samples, attributing this action to the classic role assigned to TF as FVIIa receptor. However, in the same experimental conditions, non-lipidated TF has demonstrated a complete lack of effect, which indicates that lipidization is necessary to achieve TF functionality (section 6.1 of the results).

The use of lipidated TF as a topical hemostatic agent has never been described as a single treatment for mild, severe and lethal bleedings (traumatic or surgical arterial and venous hemorrhages).

European patent EP 266993 discloses the use of non-lipidated TF as a hemostatic agent for parenteral treatment of hemorrhagic syndromes. However, the same patent discloses the important differences in activity between the non-lipidated TF claimed by EP 266993 and the lipidated TF object of the present patent application.

In fact, it is well known that lipidated TF is active in vitro conditions and their parenteral administration immediately initiates disseminated intravascular coagulation with fatal consequences. In contrast, non-lipidated TF is not active in vitro conditions, however it has been claimed (EP 266993) for treatment of coagulopathies by parenteral administration.

To date, there are not data about the effect of both, lipidated and non-lipidated TF for single topical treatment of bleeding episodes. In the present patent application, using the tail rat transection model, the inventors have demonstrated that non-lipidated TF was unable to stop bleeding. In contrast, inventors have shown for the first time, that lipidated TF is a useful hemostatic agent to treat topically all kind of hemorrhages, including in pathological (animals treated with heparin and warfarin) and in healthy conditions (control rats without alteration of coagulation). Overall, indicates that lipidated and non-lipidated TF are clearly different compounds. Consequently, the use of lipidated TF as an agent for the single topical treatment of hemorrhages is not obvious for a person skilled in the art.

On the other hand, EP 266993 was performed according to the state of the art which postulates that the serine-protease FVII is only activated when bound to its receptor, TF. Therefore, according to EP 266993 and to the state of the art, when FVII/FVIIa is not present, TF must not be active. It was unobvious to any person skilled in the art to think of TF (lipidated and non-lipidated) could be effective in the treatment of FVII deficient patients. Inventors have discovered that even in the absence of FVIIa, TF acts as a cofactor for FXa. This finding is fundamental to understand that non-lipidated TF can also act as parenteral hemostatic agent for hemorrhage in defective FVII patients.

International patent application WO 94/02172 teaches that the temporarily inhibition of one or more natural anticoagulants by systemic administration of an inhibitor of a natural anticoagulant (an antibody) can inhibit microvascular bleeding. Optionally, the inhibitor can be administered in combination with a topical administration of thrombin or lipidated TF. It is important to point out that the use of both compounds was always as optional adjuvant treatments and never as single treatment. Moreover, WO 94/02172 claims the use of these synergistic treatments only for capillary bleeding (microvascular bleeding, i.e. burns, inflamed visceral surfaces, bleeding liver surfaces . . . ), and never for severe or lethal hemorrhages caused by surgery or external trauma involving arterial and venous injury. However, the inventors of WO 94/02172 admit that, although they observed a synergistic effect when topically administering thrombin in combination with the systemic treatment, no such synergistic effect was observed when administering topically TF (WO 94/02172, FIG. 3 and page 22, lines 14-15). Moreover, the dose claimed in WO 94/02172 ranges very high, from 0.1 to 10 mg.

Contrary to WO 94/02172, the present patent application is claiming the single treatment of mild/moderate to severe/lethal arterial or venous hemorrhage with lipidated TF alone showing examples in which such treatment is effective at a 1.2 μ/ml of active protein dose for traumatic hemorrhages (see severe model in tables 24 and 25). Such a surprising and extraordinarily effective treatment has not been described until now, because it was unobvious for any person skilled in the art that lipidated TF acts as a stimulator of FXa proteolytic activity. Inventors have discovered that in the absence of FVIIa, TF acts as a cofactor for FXa, even in the absence of its well known cofactor, FVa. This finding is fundamental to understand that lipidated TF alone can act as a hemostatic agent for severe hemorrhage in healthy and pathological conditions.

U.S. Pat. No. 4,721,618 teaches that the intravenously administered synergistic mixture of phospholipids (PCPS) and FXa at high concentrations (0.2 to 0.5 U/Kg) may bypass the Factor VIII: C deficiency in a hemophilic mammal, so that the cascade process of blood clotting may continue. The suggested high concentrations of FXa are active without the need of PCPS lipid vesicles (which can enhance this activity). Also, WO 02/086118 teaches that compositions that include a mixture of at least one specific phospholipid and at least one serine protease-activated blood coagulation factor are useful for treating blood coagulation disorders decreasing the need for administered blood coagulation factors.

Furthermore, ellagic acid and other accelerators such as zeolite, silica and inorganic oxide materials have been used to enhance blood coagulation and claimed in WO 02/30479.

According to WO 02/086118, a coagulation factor is defined as a serine protease-activated blood coagulation factor (page 5, lines 13-15). Therefore, TF may not be considered as a blood coagulation factor, because TF is not a serine protease, but a specific cell surface receptor for factor VIIa.

In the present patent application the inventors have demonstrated that phospholipids (phosphatidylserine and phosphatidylcholine at different percentages and molarities) do not increase the procoagulant effect mediated by lipidated TF (table 21), which indicates that the synergistic effect claimed by U.S. Pat. No. 4,721,618 and WO 02/086118 is exclusive for serine protease-activated blood coagulation factors, but not for membrane receptors such as TF. Surprisingly, when lipidated TF was simultaneously combined with negatively charged inorganic surfaces (NCIS) a significant synergistic effect was observed in vitro and in vivo experimental conditions. NCIS used in this description are constituted by a mixture of lipids and a blood coagulation accelerator, ellagic acid. The lipids have net negative charge, what means that the lipidic mixture can include neutral or zwiterionic lipids, but it must contain a certain amount of negatively charged lipids that confers anionic character to the mixture. By way of an illustrative, non limiting example, negatively charged lipids can be sphingolipids (such as ceramide-1-phosphates, glicosilated phosphatidylethanolarnine, hydroxylated or non hydroxylated sulfatides, gangliosides) and glycerol-based lipids (such as phosphatidylserine, phosphatidylinositol, phosphatidylinositol phosphates, phosphatidic acids, phosphatidylglicerols, cardiolipins). There are commercially available NCIS such as Dade® Actin® (Dade Behring) trademark, e.g., Dade® Actin® FS.

In conclusion, the present patent application describes a new local hemostatic agent characterized by the following advantages respect to commercially available drugs:

(1) Easy topical administration
(2) No special device requirements for its topical administration
(3) Broad therapeutic focus (deficits of FV, FVII, FVIII, FIX, FX, FXI, FXII, and FXIII)
(4) Appropriate treatment to be administrated in all kind of bleeding episodes (epistaxis, dental bleeding, mucocutaneous, traumatic and surgery hemorrhages)
(5) Exerts a potent acute effect
(6) Physiological fibrin clot formation (extreme clot stability)
(7) Without side-effects
(8) Low cost treatment The main goal of WHO, FDA, EMEA and other public health authorities is to reduce the dangerous side-effects associated to the consumption of human-derived blood products blood. The present invention has been designed to cover these unmeet needs.

SUMMARY OF THE INVENTION

The role, assigned to the TF::FVIIa complex in coagulation is widely known. The TF::FVIIa complex acts as a substrate so that FX activation takes place. Recent studies have allowed identifying that the TF Lysine 165 and Lysine 166 residues interact with the Gla domain of FX, both in the activated and non-activated forms. Contrary to the TF::FVIIa complex, little is known about the interaction of TF with FX and FXa. It has only been described that TF can act as a stimulator of FXa for FVII activation. That is, the binding of FXa to TF would stimulate FVII activation which, in turn, will increase FX activation.

The inventors have discovered that the role of TF as a stimulator of FXa is much more relevant becoming critical for hemostasis (FIG. 3). It is well known that FXa at picomolar concentrations is unable to produce any effect on coagulation and platelet aggregation. Despite to the accepted role of TF as membrane receptor for FVII, the inventors have shown that TF acts also as a stimulator of FXa for enhancing its main proteolytic activity, prothrombin hydrolysis, leading to fibrin clot formation.

Surprisingly, in the presence of TF (i.e. injury or exogenous administration), FXa at picomolar concentrations, causes prothrombin hydrolysis, leading to fibrin clot formation, even in the absence of its ligand, FVII/FVIIa. Overall results, indicates that TF acts as a stimulator of FXa, and the specific binding of FXa to TF is the first step that triggers blood coagulation.

The inventors' data suggests that the quickness with which coagulation takes place is dependent on the interaction between TF and in all FXa previously described forms.

In the presence of FXa physiological concentrations (<150 pM) incapable of initiating coagulation on their own, lipidated TF is able to quickly initiate thrombin formation as result of its action as a cofactor.

These hemostasic effects are surprisingly independent of the presence of FVII and FVIIa, therefore the procoagulant effect mediated by the endogenous TF::FXa complex (FXa<150 pM) is particularly useful and relevant in factor VII-deficient samples. Nevertheless, potent hemostasic effects have also been observed in samples from patients with congenital defects of other coagulation factors, such as: FVIII (hemophilia A), FIX (hemophilia B), FXI (hemophilia C), FV, FX, FXII, and FXIII, as well as in individuals with congenital platelet disorders, such as the Bernard Soulier Syndrome and Glanzmann's Disease and Thrombocytopenic Disorders.

Therefore, this invention is based on the use of lipidated TF alone or combined with FXa and/or with NCIS as a new stimulator of FXa useful for the topical treatment of hemorrhages present in healthy individuals and in patients with hemorrhagic diathesis.

The results obtained by the inventors open the doors to the use of non-lipidated TF or a functional fragment thereof for the treatment of hemorrhaging in a FVII-deficient subject. Said treatment can be carried out by means of the use of suitable pharmaceutical administration forms for the parenteral administration of non-lipidated TF.

Therefore, in an aspect the invention relates to the use of lipidated TF, or a functional fragment thereof, in the preparation of a drug for the topical treatment of hemorrhaging in a subject.

In another aspect, the invention relates to a product comprising lipidated TF alone or combined with FXa and/or a NCIS. The use of said product as a drug or in the preparation of a drug for the treatment of hemorrhaging in a subject constitutes a further aspect of this invention.

In another aspect the invention relates to a complex formed by lipidated TF and a compound selected from FXa, an NCIS and combinations of both. The use of said complex as a drug or in the elaboration of a drug for the treatment of hemorrhaging in a subject constitutes a further aspect of this invention.

In another aspect the invention relates to a pharmaceutical composition comprising a lipidated TF, together with a pharmaceutically acceptable carrier. In a particular embodiment, said pharmaceutical composition further comprises FXa and/or an NCIS.

In another aspect the invention relates to a product comprising said pharmaceutical composition and a support. In a particular embodiment, said pharmaceutical composition further comprises FXa and/or an NCIS.

In another aspect the invention relates to the use of non-lipidated TF, or a functional fragment thereof, for the preparation of a drug for the treatment of hemorrhaging in a FVII-deficient subject. In a particular embodiment said drug is formulated in a pharmaceutical administration form suitable for the parenteral administration of non-lipidated TF.

DETAILED DESCRIPTION OF THE INVENTION

Figure 1:
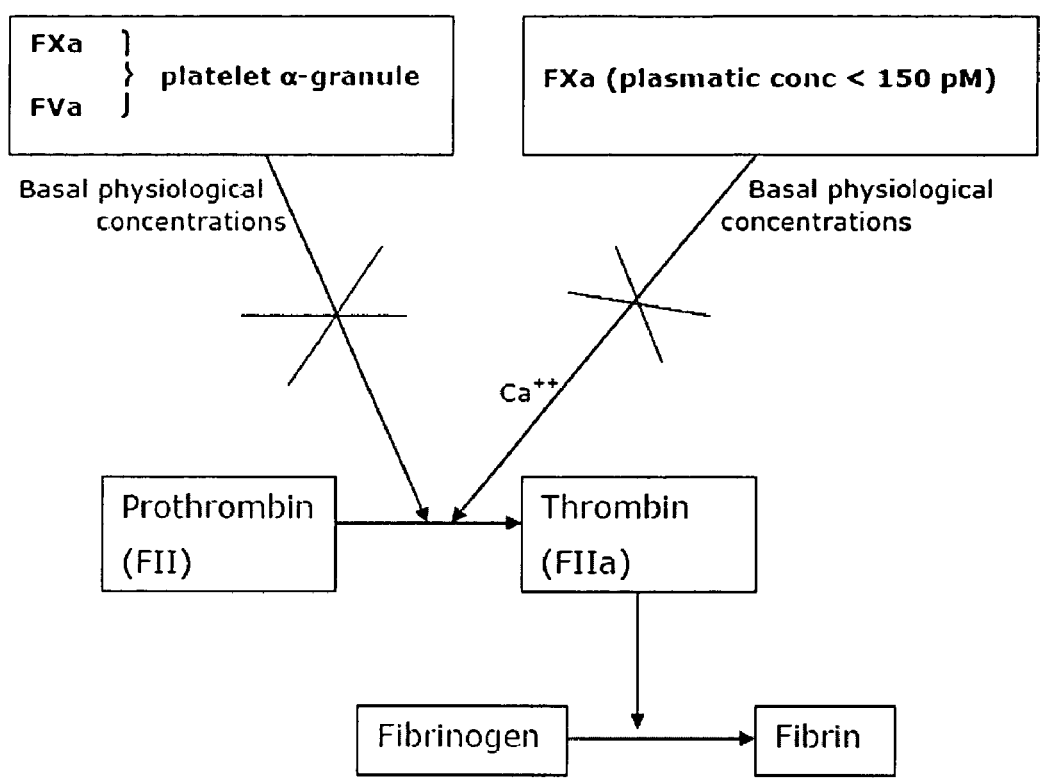
FIG. 1 is a schematic representation showing basal FXa concentrations and fibrin clot formation.
Figure 2:
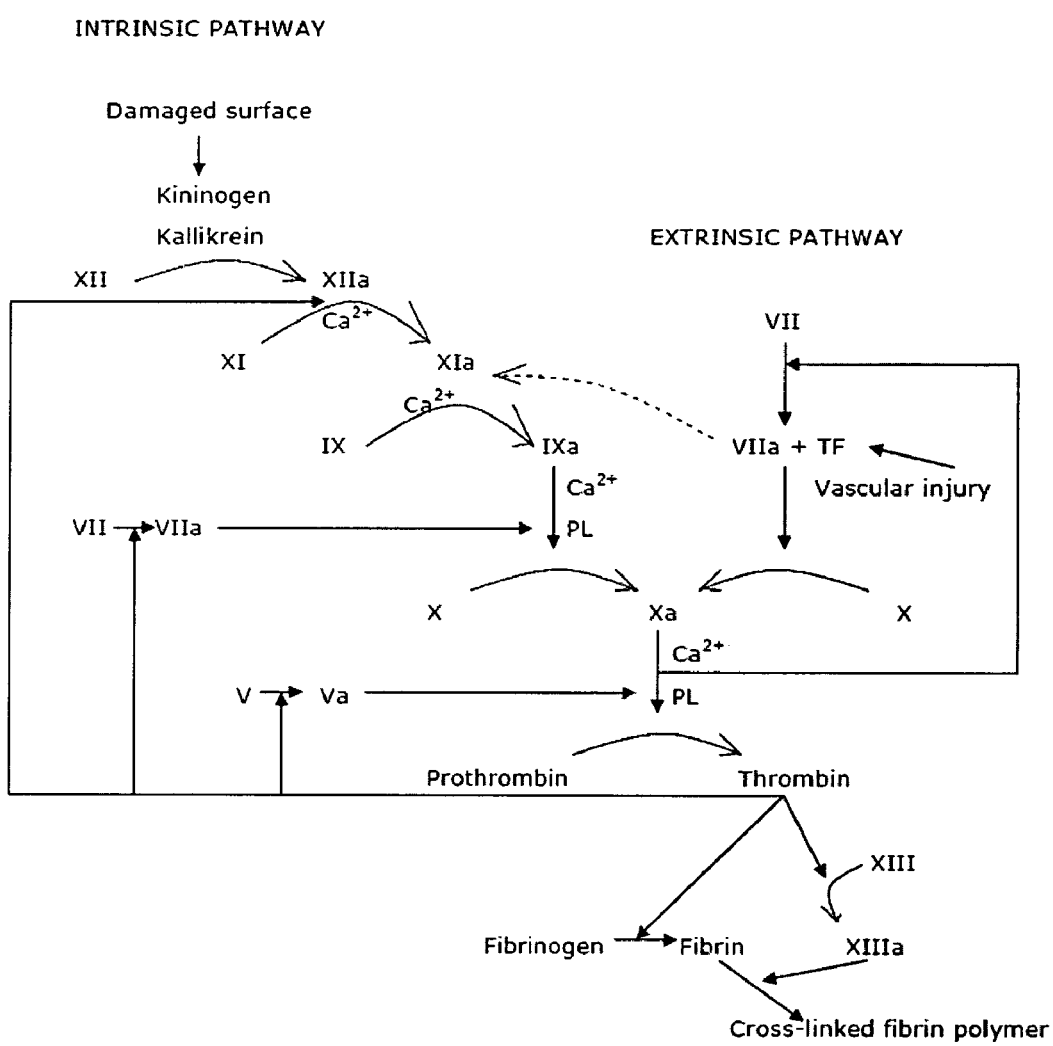
FIG. 2 is a schematic representation showing the classical intrinsic and extrinsic pathways of blood coagulation.
Figure 3:
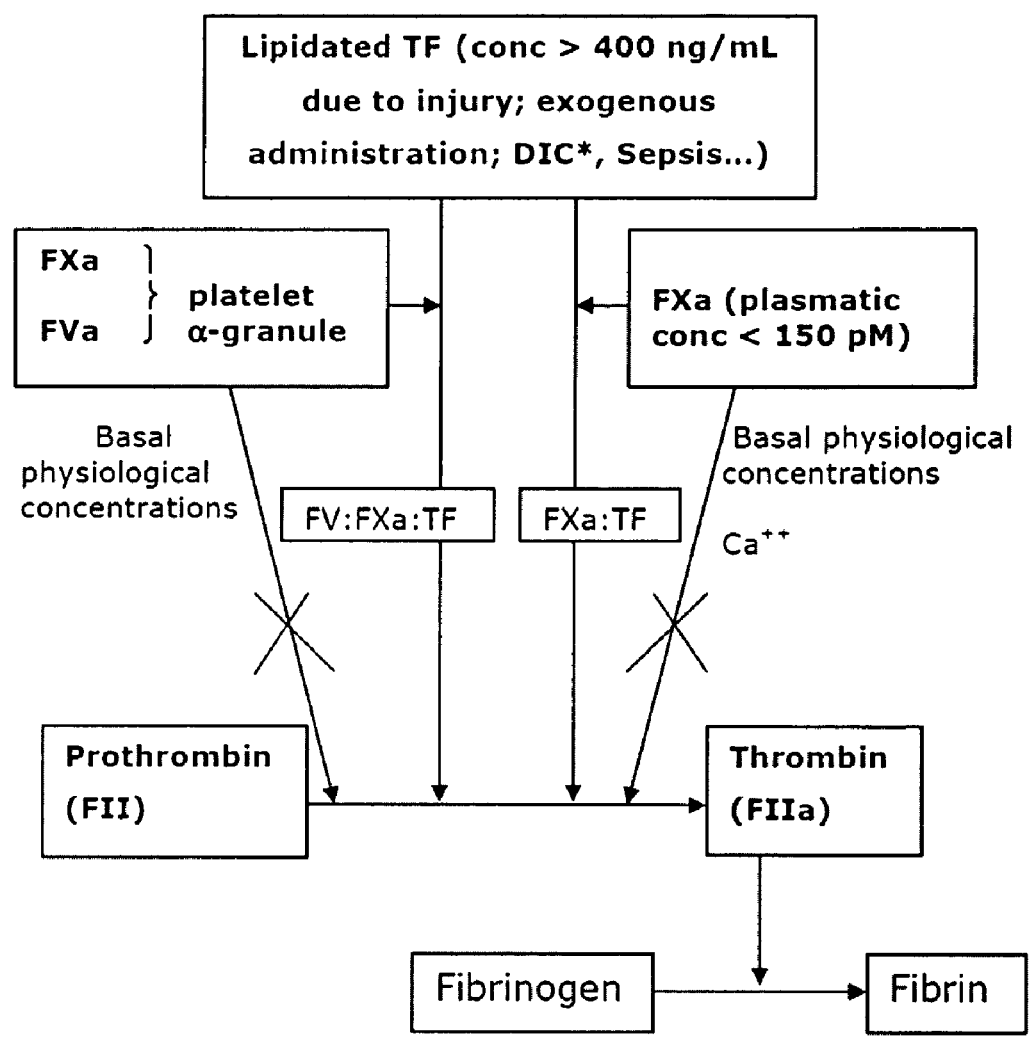
FIG. 3 is a schematic representation showing the new regulatory effect of lipidated TF as stimulator of FXa according to instant invention.

The findings herein described show for the first time that lipidated TF in the absence of its ligand, FVII/FVIIa, acts as a stimulator of FXa causing this enzyme to initiate prothrombin hydrolysis and, accordingly, for coagulation to take place. This new mechanism is particularly relevant in very low FXa concentration levels (below those considered physiological 150 pM). It is well known that there are certain platelet diseases occurring with disorders in platelet aggregation and a greater tendency of hemorrhagic episodes. Accordingly, exogenously administered lipidated TF is not only useful in congenital coagulopathies but will further allow hemostasis in congenital and acquired platelet disorders, such as Glanzmann's disease, Bernard-Soulier Syndrome and Thrombocytopenic Disorders.

The quickness with which coagulation takes place is therefore not dependent on the formation of the TF::FVIIa complex and subsequent FX activation, as has been thought until now, but the interaction of TF and FXa at physiological basal concentrations (<150 pM). The most relevant biological consequence of the formation of this interaction is the quick generation of the beginning of coagulation and that this only requires the presence of FXa at physiological concentrations present in blood and the interaction with its stimulator, TF. The process is immediately amplified as a result of the thrombin initially formed by the complex and as a result of the greater production of FXa, whether due to the TF::FVIIa complex or due to thrombin itself.

Therefore the inventors' findings clearly show that in the absence of FVIIa and in the presence of FXa at physiological concentrations (<150 pM) incapable of initiating coagulation on their own, lipidated TF quickly initiates thrombin formation as a result of its new action as a stimulator of FXa, promoting the beginning of prothrombin hydrolysis. On the other hand, the inventors' findings show that lipidated TF and FXa at low concentrations (which are not effective for exercising antihemorrhagic effects on their own) when administered together are able to quickly cause the beginning of the fibrin clot formation. The effects observed with the TF::FXa combinations, specifically with an FXa concentration <150 pM, are much better than those detected when lipidated TF is administered alone. The combination of FXa and lipidated TF with NCIS can enhance the hemostasic effect even more. The obtained results support the idea that in the presence of FXa basal concentrations present in plasma (<150 pM), incapable of generating the initial procoagulant response on their own, this response takes place when TF acts as a stimulator of Fxa.

Accordingly, lipidated TF, alone or combined with FXa and/or NCIS, can be used as new topical hemostatic agents useful for the treatment of hemorrhaging present in healthy individuals and in patients suffering from hemorrhagic diathesis.

Non-lipidated TF or a functional fragment thereof can likewise be used as a new hemostatic agent useful for treatment, preferably by parenteral administration, of hemorrhaging present in FVII-deficient patients.

I. Use of Lipidated TF in the Topical Treatment of Hemorrhages

The inventors have surprisingly found that lipidated TF increases FXa proteolytic activity and, accordingly, thrombin production [see section 1 of the results of the example included in this description]. The inventors have also observed that lipidated TF coagulates plasma and blood in healthy subjects and coagulation factor-deficient patients, including those that are FV, FVII, FVIII, FIX, FX., FXI, FXII and FXIII deficient, as well as in anticoagulated patients (by means of anticoagulant treatments with drugs such as heparin, low molecular weight heparins or coumarinic derivatives, these being a non-limiting examples), both in vitro [see, sections 1 to 5 of the results of the example included in this description] and in vivo [see sections 6 and 7 of the results of the example included in this description]. The inventors have further found that lipidated TF coagulates blood in patients suffering from platelet disorders [see section 5 of the results of the example included in this description]. These results clearly show that lipidated TF is an antihemorrhagic agent useful for topical treatment of hemorrhages in a subject.

Taking in account the state of the art, it is unobvious to think as TF as a procoagulant topical single treatment in healthy subjects or hemophilic patients (FVIII, FIX and FXI deficient).

It was absolutely unlikely in FVII-deficient patients because the TF-FVII complex cannot be formed; in FV or in FX deficient patients because the prothrombinase complex cannot be assembled; and in heparinized patients because both thrombin and FXa are blocked by antithrombin III, and in warfarin treated patients because synthesis of all vitamin K-dependent coagulation factors (FVII, FIX, and FX) are abolished.

Therefore, in an one aspect, the invention is aimed at the use of lipidated TF, or a functional lipidated fragment thereof, in the preparation of a drug for the topical treatment of hemorrhages in a subject.

TF is an integral membrane glycoprotein that is widely distributed in the animal kingdom. The TF protein has a domain structure, i.e. it is a protein with independent functional regions. Each one of the domains of the human TF apoprotein has unique structural and functional characteristics: (1) a signal peptide or a region with a 32 amino acid leader sequence that is post-translationally processed when the protein is processed from the immature to the mature form; (2) an N-glycosylated hydrophilic extracellular domain comprising about 219 terminal amino acids; (3) a fragment of about 23 amino acids, mainly hydrophobic, which are believed to be the transmembrane domain amino acids; and (4) the 21-amino acid carboxyl end which are believed to be the amino acids forming part of the protein cytoplasmic fragment. This domain structure of the human TF protein allows the production of, for example, the extracellular domain of the protein or functional fragments thereof. The amino acid sequence of the human TF protein is known and may be consulted in protein data bases such as, for example, NCBI (hTF, Access number: P13726).

The term "lipidated TF" as used herein refers to any source of TF being this TF totally or partially inserted in lipidic vesicles or cellular membranes. Illustrative, non-limiting examples of "lipidated TF" sources are: lipidated TF containing extract (whose isolation can be carried out from several tissues such as cerebral, placental and lung tissue, tissue from different animals such as sheep, cows, rabbits, dogs, human beings, etc.); purified and (re)-lipidated TF proteinaceous component (purified from an extract or from a recombinant TF), i.e. what the lipid component has been added to after its purification and which can be prepared, by way of an illustrative, non-limiting example, according to the protocol previously described by Morrisey [see the example included in this description]. In said protocol, non-lipidated TF is incorporated within phospholipid vesicles using a non-ionic detergent, such as N-octyl-beta-D-glucopyranoside, for example. The lipids that can be used in lipidated TF according to the invention may have any origin (animal, plant or synthetic). Virtually any lipid can be used in the preparation of the lipidated TF of this invention. Illustrative, non-limiting examples of lipids that can be used in the preparation of lipidated TF include phospholipids (such as phosphatidylcholine, phosphatidylserine, phosphatidylethanol-amine, etc), sphingolipids (such as ceramide, sphingosine-1-phosphate, inositolphosphate ceramide, mannosyl-inositolphosphate ceramide, mannosyl-diinositolphosphate ceramide, etc), phosphatidylinositol (such as L-α-phosphatidylinositol, L-α-lysophosphatidylinositol, etc) and phosphatidylinositol phosphates (such as L-α-[phosphatidylinositol-4-phosphate], 1,2-dioctanol-sn-glycero-3-[phosphatidylinositol-3,4,5-trisphosphate], etc). The TF proteinaceous component: lipid ratio (molar, weight or volumetric) may vary within a wide range, for example, from about 1:50,000 to about 1:3,000.

The term TF as used herein includes several wild-type TF variants and mutants maintaining at least one of the functions of the wild-type TF, advantageously, at least one of the functions of the wild-type TF relating to coagulation.

In a particular embodiment the lipidated TF used for putting the invention into practice is lipidated human TF and consists of TF obtained from tissue extracts; or TF consists in the purified proteinaceous component of tissue extracts and inserted in a lipid component (with a molar ratio protein:lipid of about 1:8700; or TF consists of recombinant TF (rTF) obtained by a process as is described, only as an illustrative but not limitative example, in U.S. Pat. No. 6,261,803. The obtention of extracts and purification of TF can be carried out from several tissues such as cerebral, placental and lung tissue, and from different animals such as sheep, cows, rabbits, dogs, and humans.

The term "functional fragment of lipidated TF" as it is used in this description includes although is not limited to peptide derivatives of TF, particularly of the proteinaceous component of TF, including mutants and variants of the proteinaceous component of wild-type TF, which maintain one or more TF functions, preferably functions relating to coagulation, for example the capability of binding to the FXa and/or to NCIS and of developing their antihemorrhagic and vessel forming function during wound healing. The amino acid sequence of said functional fragment of TF can be identical to that of a fragment of the proteinaceous component of wild-type TF or may have insertions, deletions or modifications of one or more amino acids, with the condition that at least one of the functions of wild-type TF are preserved, advantageously at least one function related to coagulation. For the sake of simplicity, the term "lipidated TF" as it is used herein includes any functional fragment of lipidated TF.

The proteinaceous component of the TF used in carrying out this invention may further be part of a fusion protein. In this sense, said fusion protein may contain a region A, consisting of the TF protein or a functional fragment of said TF protein, bound to a region B consisting of another fragment of TF. Said region B is bound to the amino-terminus region of said TF protein or of said fragment of the TF protein, or alternatively said region B may be bound to the carboxyl-terminus region of said TF protein or of said fragment of the TF protein. Both regions A and B may be directly bound or bound through a linker polypeptide between said regions A and B. The fusion protein may be obtained either by chemical synthesis or by means of gene expression of the nucleotide sequence encoding for said fusion protein in suitable host cells.

The term "topical treatment" as used herein refers to the application of the treatment directly at the site where it is required, for example, in discontinuous sections of skin (cuts, etc.) and vascular tissue (ruptured vessels, etc.).

According to this invention and as shown in the example included in this description, lipidated TF acts as a stimulator of FXa increasing its proteolytic activity, and accordingly prothrombin production, and it can therefore be used to treat or correct hemorrhagic disorders, particularly those hemorrhagic disorders associated with hemorrhagic diathesis.

The term "hemorrhagic diathesis" refers to the process causing a hemostasic disorder and which as a result gives rise to the occurrence of a hemorrhagic syndrome which may occasionally occur with extended and excessive bleeding. Hemorrhagic diathesis may be caused by a congenital or acquired coagulopathy and/or by a congenital and acquired platelet disorder.

The term "coagulopathy" refers to a coagulation factor disorder. This disorder may be due to a specific coagulation factor deficiency or deficit, the consequence of which will be the occurrence of a hemorrhagic syndrome, or due to a coagulation factor disorder. The coagulopathy may generally be a congenital coagulopathy or an acquired coagulopathy.

As illustrative, non-limiting examples of congenital coagulopathies, deficiencies of coagulation factors selected from FV, FVII, FVIII, FIX, FX, FXII, FXIII and their combinations, can, be mentioned.

Acquired coagulopathies may have different origins. Illustrative examples include coagulation factor synthesis deficiencies in severe hepatic failure, anticoagulant therapy (such as heparin, low molecular weight heparins, warfarin, coumarin derivatives, dicoumarins, etc.). An alternative mechanism is based on an exaggerated consumption of coagulation factors such that they are not available to form the clot in a bleeding lesion. This mechanism occurs in the disseminated intravascular coagulation syndrome or coagulopathy due to consumption occurring in multiple illnesses such as in severe sepsis damaging the microcirculation endothelium activating platelets and coagulation factors with the formation of multiple microthrombi; in blood invasion by TF such as placental release; in the retention of a dead fetus; in multiple traumas with the crushing of tissues; in poisonous snake bites, etc. In vasculitis, parietal and endothelial damage releases coagulation activators. The consumption of coagulation factors is worsened by lysis of the fibrin of numerous microthrombi due to the action of plasmin with PDF release, which are antiplatelets and anticoagulants.

The term "platelet disorder" refers to a disorder both in the number and in functional ability of platelets, the result of which is the occurrence of a hemorrhagic syndrome. Said platelet disorder may be congenital or acquired.

In a particular embodiment, said platelet disorder is a congenital platelet disorder. Illustrative, non-limiting examples of congenital platelet disorders include Glanzmann's disease, Bernard Soulier disease, Bolin-Jamieson syndrome, Wiskott-Aldrich syndrome, Paris-Trousseau-Jacobsen syndrome, X chromosome thrombocytopenia, Gray platelet syndrome, Sebastian syndrome and Fanconi anenia.

In another particular embodiment said platelet disorder is an acquired platelet disorder. Illustrative, non-limiting examples of acquired platelet disorders include myeloproliferative disorders, such as thrombocythemia, polycythemia, chronic myelocytic leukemia, etc.; there are functional platelet disorders in myeloid metaplasia with increased bleeding time, glass bead retention defects, platelet aggregation defect, abnormal release, and platelet factor III defect. Functional platelet defects have been found in dysproteinemias in scurvy and in congenital heart disease and cirrhosis.

The terms "acquired coagulopathy" and "acquired platelet disorder" refers to the origin of disorder, which may be iatrogenic or secondary to other disease.

The term "subject" as used herein includes any member of an animal species, including the human species; by way of an illustrative, non-limiting example, said subject can be a mammal, such as a primate, a domestic animal, a rodent, etc., said subject is preferably a man or woman of any age and race. In a particular embodiment said subject is a human being with no history of hemostasis disorders, such as an individual having no coagulopathies or platelet disorders. In another particular embodiment said subject is a human being having a history of hemostasis disorders, such as an individual having hemorrhagic diathesis, for example, a coagulopathy, such as a congenital or acquired coagulopathy, or a platelet disorder, such as a congenital or acquired platelet disorder.

Therefore, in a particular embodiment, the invention relates to the use of lipidated TF in the preparation of a drug for the topical treatment of hemorrhaging in a human being with no history of hemostasis disorders. In another particular embodiment the invention relates to the use of lipidated TF in the preparation of a drug for the topical treatment of hemorrhaging in a human being having a hemorrhagic diathesis.

For administration to the subject, the lipidated TF will be formulated in a pharmaceutical form suitable for its topical administration for topical (local) treatment of hemorrhaging. Illustrative, non-limiting examples of said pharmaceutical forms include aerosols, solutions, suspensions, emulsions, gels, salves, creams, dressings, patches, ointments, mouthwashes, etc. To that end the pharmaceutical formulation comprising lipidated TF will include the pharmaceutically acceptable carriers and excipients required for preparing the chosen pharmaceutical administration form (for more information see the section relating to "Pharmaceutical Composition" in this description).

The lipidated TF dose to be administered to the subject may vary within a very broad range, for example, between about 0.01 μg of active protein/ml and 100 μg of active protein/ml. The lipidated TF dose to be administered will depend on several factors, including among them the features of the TF protein used, such as for example, its activity and biological half life, concentration of the TF protein in the formulation, the clinical condition of the subject or patient, the hemorrhagic disorder to be treated, etc. (for more information see the section relating to "Pharmaceutical Composition" in this description).

II. Combination Products and Applications

II.1 Lipidated TF+FXa

As it is known, in the extrinsic pathway of blood coagulation TF binds to circulating FVII/FVIIa to form the TF::FVII complex and, in the presence of calcium, to act as a substrate so that FX activation takes place. Activation of the extrinsic pathway involves the interaction of TF with its ligand, FVII/FVIIa. This complex, TF::FVIIa, acts as a substrate so that FX activation by FVIIa takes place. Now the inventors have surprisingly found that lipidated TF together with FXa, even in FVII-deficient subjects, induces coagulation, such that lipidated TF acts as an FXa stimulator, allowing this serine protease to initiate prothrombin hydrolysis, to produce prothrombin and for the origin of coagulation to take place. As used herein, "FXa", refers to a protein, particularly a serine protease, which in its active form is responsible for initiating prothrombin hydrolysis and accordingly gives rise to the beginning of coagulation. This proteolysis is performed by FXa binding to the activated platelet surface and, in the presence of FVa and ionic calcium, hydrolyzing prothrombin.

More specifically, the inventors have surprisingly found that the combination of lipidated TF and FXa, even at such low FXa concentrations that they are incapable of inducing coagulation on their own, coagulates plasma [see, for example, sections 1 (1.5), and 2 of the results of the example included in this description].

Therefore, in another aspect, the invention relates to a product comprising (i) lipidated TF and (ii) FXa. Based on the previously mentioned results, said product can be used as a drug, and it can particularly be used in the treatment of hemorrhaging, for example, in the topical treatment of hemorrhaging, in a subject. Said components (i) and (ii) can be together or separate. In a particular embodiment, the lipidated TF used in the preparation of this product is lipidated human TF.

In a particular embodiment, the invention provides a product comprising (i) lipidated TF and (ii) FXa. Both components can be combined and be together in the same composition before their administration to the subject.

In another particular embodiment, the invention provides a product comprising, separately, (i) lipidated TF and (ii) FXa. In another particular embodiment the invention provides a product comprising, separately, (i) lipidated TF and (ii) FXa, as a combination for their simultaneous or successive administration to a subject. The combined administration of said components (i) and (ii) to the subject can be carried out simultaneously or sequentially, spaced out in time, in any order, i.e. first lipidated TF and then FXa can be administered, or viceversa. Alternatively, said lipidated TF and FXa can be simultaneously administered.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. For more information see the section relating to the "Pharmaceutical Composition" of this description.

The lipidated TF and FXa dose to be administered to the subject may vary within a wide range. By way of illustration, the lipidated TF dose to be administered may be comprised between about 0.01 µg of active protein/ml and 100 µg of active protein/ml. Also, by way of illustration, the FXa dose to be administered may be comprised between about 17 pM and 17 nM (0.001 µg of active protein/ml and 10 µg of active protein/ml). Generally, the lipidated TF and FXa doses to be administered will depend on several factors, including the characteristics of the TF protein used and the FXa, such as for example, their activity and biological half life, the concentration of the FXa and TF protein in the formulation, the clinical condition of the subject or patient, the hemorrhagic disorder to be treated, etc. (for more information see the section relating to the "Pharmaceutical Composition" of this description).

The weight ratio of the lipidated TF and FXa present in said product may vary within a wide range; by way of illustration, said TF:FXa weight ratio is comprised between $10^6$:1 and 10:1, although other weight ratios are also possible; in a particular embodiment said product of the invention comprises lipidated TF and FXa at a weight ratio of 1 to 0.001, i.e. for each milligram of TF protein there is 1 microgram FXa protein present in the mixture.

The use of the product previously defined as a drug, specifically the use of said product in the preparation of a drug for the treatment of hemorrhaging in a subject, particularly for the topical treatment of hemorrhaging in a subject, constitute further aspects of this invention.

II.2 Lipidated TF+NCIS

The inventors have also surprisingly found that the combination of lipidated TF and negatively charged inorganic surfaces (NCIS) coagulates plasma and blood of healthy subjects and of coagulation factor-deficient patients both in vitro [see sections 1 (1.4), 2 (2.2), 3 (3.4), 4 (4.2) and 5 (5.2 and 5.4) of the results of the example included in this description] and in vivo [see sections 6.1 of the results of the example included in this description].

The term "negatively charged inorganic surface" or "NCIS" as used in this description are constituted by a mixture of lipids and a blood coagulation accelerators, such as ellagic acid, zeolite, silica, inorganic oxide materials, etc. The lipids have net negative charge, what means that the lipidic mixture can include neutral or zwiterionic lipids, but it must contain a certain amount of negatively charged lipids that confers anionic character to the mixture. By way of an illustrative, non limiting example, negatively charged lipids can be sphingolipids (such as ceramide-1-phosphates, glicosilated phosphatidylethanolamine, hydroxylated or non hydroxylated sulfatides, gangliosides, etc.) and glycerol-based lipids (such as phosphatidylserines, phosphatidylinositols, phosphatidylinositol phosphates, phosphatidic acids, phosphatidylglicerols, cardiolipins). In the present patent application, the commercially available Dade® Actin® products (Dade Behring, trademark) was used as a source of NCIS.

Therefore, in another aspect, the invention relates to a product comprising (i) lipidated TF and (ii) a NCIS. Based on the previously mentioned results, said product can be used as a drug, and it can particularly be used in treatment of hemorrhages, for example, in the topical treatment of hemorrhaging, in a subject. Said components (i) and (ii) can be together or separate.

In a particular embodiment, the invention provides a product comprising (i) lipidated TF and (ii) a NCIS. Both components can be combined and be together in the same composition before their administration to the subject.

In another particular embodiment, the invention provides a product comprising, separately, (i) lipidated TF and (ii) NCIS. In another particular embodiment the invention provides a product comprising, separately, (i) lipidated TF and (ii) NCIS, as a combination for their simultaneous or successive administration to a subject. The combined administration of said components (i) and (ii) to the subject can be carried out simultaneously or sequentially, spaced out in time, in any order, i.e. first the lipidated TF and then the NCIS can be administered, or viceversa. Alternatively, said lipidated TF and NCIS can be simultaneously administered.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. For more information see the section relating to the "Pharmaceutical Composition" of this description.

The lipidated TF and NCIS dose to be administered to the subject may vary within a wide range. By way of illustration, the lipidated TF dose to be administered may be comprised between about 0.01 µg of active protein/ml and 100 µg of active protein/ml. Also, by way of illustration, the NCIS dose (by volume) to be administered may be comprised between about 0.1 and 100 µl for each µg of lipidated TF actived protein. Generally, the lipidated TF and NCIS doses to be administered will depend on several factors, including the characteristics of the TF protein used and the NCIS, such as for example, their activity and biological half life, the concentration of the TF protein and NCIS in the formulation, the clinical condition of the subject or patient, the hemorrhagic disorder to be treated, etc. (for more information see the section relating to the "Pharmaceutical Composition" of this description).

The weight/volume (w/v) ratio of lipidated TF and NCIS present in said product may vary within a wide range; by way of illustration said lipidated TF:NCIS w/v ratio is comprised between 1:1 and 1:$10^6$, although other w/v ratios are also possible; in a particular embodiment, said product of the invention comprises between 0.1 and 100 µl of NCIS for each µg of lipidated TF active protein.

The use of the product previously defined as a drug, specifically the use of said product in the preparation of a drug for the treatment of hemorrhages in a subject, particularly for the topical treatment of hemorrhaging in a subject, constitute further aspects of this invention.

II.3 Lipidated TF+FXa+NCIS

The inventors have also surprisingly found that the combination of lipidated TF, FXa and NCIS coagulates plasma and blood of healthy subjects and of coagulation factor-deficient patients in vitro [see sections 1 (1.6) and 2 (2.2) of the results of the example included in this description].

Therefore, in another aspect, the invention relates to a product comprising (i) lipidated TF, (ii) FXa and (iii) NCIS. Based on the previously mentioned results, said product can be used as a drug, and it can particularly be used in the treatment of hemorrhages, for example, in the topical treatment of hemorrhaging, in a subject. Said components (i), (ii) and (iii) can be together or separate. Alternatively, two of the components can be together, for example, (i)+(ii), (i)+(iii) or (ii)+(iii), and the third one separate.

In a particular embodiment, the invention provides a product comprising (i) lipidated TF, (ii) FXa and (iii) NCIS. Said components can be combined and be together in the same composition before their administration to the subject.

In another particular embodiment, the invention provides a product comprising, separately, (i) lipidated TF, (ii) FXa and (iii) NCIS. In another particular embodiment the invention provides a product comprising, separately, (i) lipidated TF, (ii) FXa and (iii) NCIS, as a combination for their simultaneous or successive administration to a subject. The combined administration of said components (i), (ii) and (iii) to the subject can be carried out simultaneously or sequentially, spaced out in time, in any order, i.e. first the lipidated TF, then the FXa, and then the NCIS can be administered, or first the lipidated TF, then the NCIS, and then the FXa can be administered, or first the FXa, then the lipidated TF, and then the NCIS can be administered, or first the FXa, then the NCIS, and then the lipidated TF can be administered, or first the NCIS, then the FXa, and then the lipidated TF can be administered, or first the NCIS, then the lipidated TF and then the FXa can be administered. Alternatively, any two of said components can be mixed in the same composition and be administered together while the third one can be added before or after said binary component composition. In another alternative embodiment said lipidated TF, FXa and NCIS are simultaneously administered.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. For more information see the section relating to the "Pharmaceutical Composition" of this description.

The lipidated TF, FXa and NCIS dose to be administered to the subject may vary within a wide range. By way of illustration, the lipidated TF dose to be administered may be comprised between about 0.01 µg of active protein/ml and 100 µg of active protein/ml. Also, by way of illustration, the FXa dose to be administered may be comprised between about 17 pM and 170 nM (0.001 µg of protein and 10 µg of protein/ml). Additionally, by way of illustration, the NCIS dose (by volume) to be administered may be comprised between about 0.1 and 100 µl for each µg of lipidated TF active protein. Generally, the lipidated TF, FXa and NCIS doses to be administered will depend on several factors, including the characteristics of the TF protein, FXa and NCIS used, such as for example, their activity and biological half life, the concentration of the TF protein, FXa and NCIS in the formulation, the clinical condition of the subject or patient, the hemorrhagic disorder to be treated, etc. (for more information see the section relating to the "Pharmaceutical Composition" of this description).

The weight ratio of the lipidated TF, FXa and NCIS present in said product may vary within a wide range, as previously mentioned in sections II.1 and II.2; nevertheless, in a particular embodiment, said product of the invention comprises lipidated TF:FXa:NCIS at a 1:0.001:100 (w:w:v) ratio.

The use of the product previously defined as a drug, specifically the use of said product in the preparation of a drug for the treatment of hemorrhages in a subject, particularly for the topical treatment of hemorrhaging in a subject, constitute further aspects of this invention.

III. Complexes and Applications

III.1 TF::FXa complex

As previously mentioned (see section II.1 of this description), the inventors have found that the combination of lipidated TF and FXa, even at such low FXa concentrations that they are incapable of inducing coagulation on their own, coagulates plasma. Though it is not intended to be linked to any theory, it is thought that the administration, either combined or separate (in any order), of said lipidated TF and FXa gives rise to the formation of a complex that is able to exercise the therapeutic effect (antihemorrhagic, particularly, topical antihemorrhagic) observed at the site where said therapeutic effect must be exercised.

Therefore, in another aspect, the invention relates to a complex, identified as TF: :FXa in this description, comprising lipidated TF and FXa. Although for the sake of simplicity said complex is represented as TF::FXa, said complex could actually be formed by several units of each of said components; all these possibilities are within the scope of the invention. In view of the previously mentioned results, said complex can be used as a drug, and it can particularly be used in the treatment of hemorrhages for example, in the topical treatment of hemorrhaging, in a subject. In a particular embodiment, the lipidated TF used in the preparation of this complex is lipidated human TF.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. For more information see the section relating to the "Pharmaceutical Composition" of this description.

The lipidated TF and FXa doses present in said complex to be administered to the subject may vary within a wide range. Generally, said doses correspond to the doses previously mentioned in section II.1 relating to a product comprising lipidated TF and FXa.

The weight ratio of the lipidated TF and FXa present in said TF::FXa complex may vary within a wide range; although it generally corresponds to that previously mentioned in II.1 relating to a product comprising lipidated TF and FXa.

The use of the complex previously defined as a drug, specifically the use of said complex in the preparation of a drug for the treatment of hemorrhaging in a subject, particularly for the topical treatment of hemorrhages in a subject, constitute further aspects of this invention.

III.2 TF::NCIS Complex

As previously mentioned (see section II.2 of this description), the inventors have found that the combination of lipidated TF and NCIS coagulates plasma and blood in healthy subjects and in coagulation factor-deficient patients both in vitro and in vivo. Though it is not intended to be linked to any theory, it is thought that the administration, either combined or separate (in any order), of said lipidated TF and NCIS gives rise to the formation of a complex that is able to exercise the therapeutic effect (antihemorrhagic, particularly, topical antihemorrhagic) observed at the site where said therapeutic effect must be exercised.

Therefore, in another aspect, the invention relates to a complex, identified as TF::NCIS in this description, comprising lipidated TF and NCIS. Although for the sake of simplicity said complex is represented as TF::NCIS, said complex could actually be formed by several units of each of said components; all these possibilities are within the scope of the invention. In view of the previously mentioned results, said complex can be used as a drug, and it can particularly be used in the treatment of hemorrhages for example, in the topical treatment of hemorrhaging, in a subject. In a particular embodiment, the lipidated TF used in the preparation of this complex is lipidated human TF.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. For more information see the section relating to the "Pharmaceutical Composition" of this description.

The lipidated TF and NCIS doses present in said complex to be administered to the subject may vary within a wide range. Generally, said doses correspond to the doses previously mentioned in section II.2 relating to a product comprising the combination of lipidated TF and NCIS.

The w/v ratio of the lipidated TF and NCIS present in said TF::NCIS complex may vary within a wide range; although it generally corresponds to that previously mentioned in II.2 relating to a product comprising lipidated TF and NCIS.

The use of the complex previously defined as a drug, specifically the use of said complex in the preparation of a drug for the treatment of hemorrhages in a subject, particularly for the topical treatment of hemorrhaging in a subject, constitute further aspects of this invention.

III.3 Lipidated TF::FXa::NCIS Complex

As previously mentioned (see section II.3 of this description), the inventors have found that the combination of lipidated TF, FXa and NCIS coagulates plasma. Though it is not intended to be linked to any theory, it is thought that the administration, either combined or separate (in any order), of said lipidated TF, FXa and NCIS gives rise to the formation of a complex that is able to exercise the therapeutic effect (antihemorrhagic, particularly, topical antihemorrhagic) observed at the site where said therapeutic effect must be exercised. Therefore in another aspect, the invention relates to a complex, identified as TF::FXa::NCIS in this description, comprising lipidated TF, FXa and NCIS. Although for the sake of simplicity said complex is represented as TF::FXa::NCIS, said complex could actually be formed by several units of each of said components, as well as by any possibility of interactions between said components, for example, TF::NCIS::FXa, FXa::NCIS::TF, FXa::TF::NCIS, NCIS::TF::FXa or NCIS::FXa::TF; all these possibilities are within the scope of the invention. In view of the previously mentioned results, said complex can be used as a drug, and it can particularly be used in the treatment of hemorrhaging, for example, in the topical treatment of hemorrhaging, in a subject. In a particular embodiment, the lipidated TF used in the preparation of this complex is lipidated human TF.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. For more information see the section relating to the "Pharmaceutical Composition" of this description.

The lipidated TF, FXa and NCIS present in said complex to be administered to the subject may vary within a wide range. Generally, said doses. correspond to the doses previously mentioned in section II.3 relating to a product comprising the combination of lipidated TF, FXa and NCIS.

The ratio of lipidated TF, FXa and the NCIS present in said TF::FXa::NCIS complex may vary within a wide range; although it generally corresponds to that previously mentioned in II.3 relating to a product comprising lipidated TF, FXa and NCIS.

The use of the complex previously defined as a drug, specifically the use of said complex in the preparation of a drug for the treatment of hemorrhages in a subject, particularly for the topical treatment of hemorrhages in a subject, constitute further aspects of this invention.

IV. Pharmaceutical Composition

As previously mentioned, lipidated TF can be used as an antihemorrhagic agent, particularly, as an antihemorrhagic agent for topical application. Therefore in another aspect, the invention relates to a pharmaceutical composition, hereinafter, pharmaceutical composition of the invention, comprising lipidated TF together with a pharmaceutically acceptable carrier. In a particular embodiment, the lipidated TF is lipidated human TF.

For its administration to a subject, the previously defined product will be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. A review of the different pharmaceutical administration forms of drugs in general, and of their preparation processes, can be found in the book "Tratado de Farmacia Galénica" (*"Galenic Pharmacy Treatise"*), by C. Faulíi Trillo, 1$^{st}$ Edition, 1993, Luzán 5, S.A. of Ediciones.

Although different pharmaceutical administration forms of lipidated TF could be used, administering said compound topically is most advantageous in practice, therefore said lipidated TF will be formulated in a pharmaceutical form suitable for its topical administration. Illustrative, non-limiting examples of said pharmaceutical forms include aerosols, solutions, suspensions, emulsions, gels, salves, creams, dressings, patches, ointments, mouthwashes, etc. To that end the pharmaceutical formulation comprising lipidated TF will include the pharmaceutically acceptable carriers and excipients required for preparing the pharmaceutical administration form of lipidated TF for topical administration.

Therefore, in a particular embodiment, the pharmaceutical composition of the invention is a pharmaceutical composition for the topical administration of a lipidated TF, comprising lipidated TF and a pharmaceutically acceptable carrier suitable for the topical administration of said lipidated TF.

Lipidated TF will be present in the pharmaceutical composition of the invention in a therapeutically effective amount. Said amount may vary within a wide range, for example, between about 0.01 μg of active protein/mil and 100 μg of active protein/ml.

In another particular embodiment the pharmaceutical composition of the invention comprises:

a) a product comprising (i) lipidated TF and (ii) FXa, together with a pharmaceutically acceptable carrier; or b) separately, (i) lipidated TF together with a pharmaceutically acceptable carrier, and (ii) FXa together with a pharmaceutically acceptable carrier; or c) a product comprising (i) lipidated TF and (ii) an NCIS, together with a pharmaceutically acceptable carrier; or d) separately, (i) lipidated TF together with a pharmaceutically acceptable carrier, and (ii) an NCIS together with a pharmaceutically acceptable carrier; or e) a product comprising (i) lipidated TF, (ii) FXa and (iii) an NCIS, together with a pharmaceutically acceptable carrier; or f) separately, (i) lipidated TF together with a pharmaceutically acceptable carrier, (ii) FXa together with a pharmaceutically acceptable carrier, and (iii) an NCIS together with a pharmaceutically acceptable carrier; or g) a TF::FXa complex together with a pharmaceutically acceptable carrier; or h) a TF::NCIS complex together with a pharmaceutically acceptable carrier; or i) a TF::FXa::NCIS complex together with a pharmaceutically acceptable carrier.

The previously defined pharmaceutical composition of the invention contains, as can be seen, lipidated TF alone or combined with FXa and/or NCIS or forming complexes with FXa and/or NCIS, as the active ingredient. In a particular embodiment, the lipidated TF present in the previously defined pharmaceutical composition of the invention is lipidated human TF.

Also, in a particular embodiment, the previously defined pharmaceutical composition of the invention will be formulated in a pharmaceutical form for the topical administration of the active ingredient (lipidated TF alone or combined with FXa and/or NCIS or forming complexes with FXa and/or NCIS). Illustrative, non-limiting examples of said pharmaceutical forms include aerosols, solutions, suspensions, emulsions, gels, salves, creams, dressings, patches, ointments, mouthwashes, etc. To that end, the pharmaceutical formulation comprising the previously mentioned active ingredient will include the pharmaceutically acceptable carriers and excipients required for the preparation of the pharmaceutical administration form of said active ingredient by topical administration.

The active ingredient will be present in the pharmaceutical composition of the invention in a therapeutically effective amount. The active ingredient dose to be administered to a subject will depend, among other factors, on the severity of the pathology said subject suffers from, on the chosen pharmaceutical administration form, etc. For this reason the doses mentioned in this invention must be considered only as guides for a person skilled in the art, and this person must adjust the doses according to the previously mentioned variables. Nevertheless, the pharmaceutical composition of the invention can be administered one or more times a day for preventive or therapeutic purposes.

The pharmaceutical composition of the invention can be used together with other additional drugs useful in the prevention and/or treatment of a hemorrhagic diathesis (e.g., coagulation factors, human plasma, etc.) to provide a combination therapy. Said additional drugs can be part of the same pharmaceutical composition or, alternatively, they can be provided in the form of a separate composition for their simultaneous or successive (sequential in time) administration with respect to the administration of the pharmaceutical composition of the invention.

V. Supported Pharmaceutical Composition

The pharmaceutical composition of the invention can be placed on a support. Therefore in another aspect the invention relates to a product comprising the pharmaceutical composition of the invention and a support. The term "support" as used herein refers to a substrate of suitable material allowing depositing the pharmaceutical composition of the invention thereon, its being carried and its release at the desired site, for example, in the site where the pharmaceutical composition of the invention exercises its therapeutic effect. Said support can be a solid support or a non-solid support, for example, a liquid support or a gaseous support. Illustrative, non-limiting examples of solid supports include dressings, band-aids, compresses, plasters, etc. Illustrative, non-limiting examples of liquid supports include gels, sprays, mouthwashes, etc.

Illustrative, non-limiting examples of gaseous supports include air, propellants, etc. In a particular embodiment the pharmaceutical composition of the invention deposited on said support comprises:

(a) (i) a support, (ii) a product comprising lipidated TF and FXa, together with a pharmaceutically acceptable carrier, (iii) a product comprising lipidated TF and an NCIS, together with a pharmaceutically acceptable carrier and (iv) a product comprising lipidated TF, FXa and an NCIS, together with a pharmaceutically acceptable carrier; or (b) a TF::FXa complex, together with a pharmaceutically acceptable carrier, or (c) a TF::NCIS complex, together with a pharmaceutically acceptable carrier, or (d) a TF::FXa::NCIS complex, together with a pharmaceutically acceptable carrier.

In a particular embodiment, the lipidated TF present in the pharmaceutical composition of the invention is lipidated human TF.

This product comprising the pharmaceutical composition of the invention deposited on a support can be obtained by conventional methods, for example, by mixing the pharmaceutical composition of the invention and the support. The interaction between the pharmaceutical composition of the invention and the support can be a physical or chemical interaction, depending on the nature of the components of the pharmaceutical composition of the invention and on the support used.

VI. Use of Non-lipidated TF for the Treatment of Hemorrhages

The results obtained in the assays carried out by the inventors clearly show that TF:

increases the proteolytic activity of FXa, and accordingly thrombin production, coagulates the plasma and blood of healthy subjects and of coagulation factor-deficient patients, including FVII-deficient blood, coagulates the blood of patients suffering from platelet disorders, and stops in vivo severe and lethal hemorrhages in different animal models.

Therefore, these results as a whole clearly show that lipidated TF is an antihemorrhagic agent useful for the treatment of hemorrhages in healthy subjects and coagulation factor deficiencies, including FVIII, FIX, FXI, FXIII, FVII, F, and FX deficient patients.

European patent EP 266993 discloses the use of non-lipidated TF in the treatment of hemorrhaging, particularly, in the treatment of hemorrhaging due to a deficiency of a coagulation factor, specifically of a coagulation factor chosen from FVIII, FIX, FXI or FXIII. However, said patent neither discloses nor suggests the possibility of using non-lipidated TF in the treatment of hemorrhaging due to FVII deficiency.

The discovery now made by the inventors relating to the role of TF as an FXa proteolytic activity stimulating agent regardless of whether the subject is FVII-deficient or not, allows establishing the possibility of using non-lipidated TF, or a functional non-lipidated fragment thereof, in the treatment of hemorrhaging in an FVII-deficient subject.

Therefore, in another aspect the invention relates to the use of non-lipidated TF, or a functional non-lipidated fragment thereof, for the preparation of a drug for the treatment of hemorrhaging in an FVII-deficient subject.

The term "non-lipidated TF" as used herein refers to the purified TF (without the plasmatic lipidic membranes). The term TF as used herein includes wild-type TF variants and mutants maintaining at least one of the wild-type TF functions, advantageously at least one of the wild-type TF functions relating to coagulation. The isolation and purification of TF can be carried out from several tissues such as cerebral, placental and lung tissue, tissue from different animals such as sheep, cows, rabbits, dogs, human beings, etc. TF can also be recombinant TF (rTF) obtained by a process as is described, only as an illustrative but not limitative example, in U.S. Pat. No. 6,261,803. In a particular embodiment, the non-lipidated TF used for putting the invention into practice is non-lipidated human TF and consists of the proteinaceous component of a TF isolated and purified from human tissue completely depleted from plasmatic lipidic membranes.

The term "functional fragment of non-lipidated TF" as used in this description, includes, although it is not limited to, peptide derivatives of TF, particularly of the proteinaceous component of TF, including mutants and variants of the proteinaceous component of wild-type TF, which maintain one or more TF functions, preferably functions relating to coagulation, for example the capability of binding to the FXa and/or to NCIS and of developing their antihemorrhagic and vessel forming function during wound healing. The amino acid sequence of said functional fragment of TF can be identical to that of a fragment of the proteinaceous component of wild-type TF or may have insertions, deletions or modifications of one or more amino acids, with the condition that at least one of the functions of wild-type TF are preserved, advantageously at least one function relating to coagulation. For the sake of simplicity, the term "non-lipidated TF" as it is used herein includes any functional fragment of non-lipidated TF.

The non-lipidated TF can be obtained by conventional methods. By way of illustration, the proteinaceous component of TF is disassociated from the lipid component by means of extraction with organic solvents. Illustrative examples of said organic solvent include pyridine, ethanol, heptane-butanol mixtures, etc. The proteinaceous component of TF can be purified by means of conventional chemical processes. Examples of said chemical processes include treatment with detergents, for example deoxycholate, Triton X-100, etc., gel filtration and preparative electrophoresis in polyacrylamide gels in the presence of sodium dodecyl sulfate, the use of concavalin A bound to a Sepharose column, the use of affinity columns using antibodies for the proteinaceous component (protein) of TF, etc.

For its administration to an FVII-deficient subject, non-lipidated TF will be formulated in a pharmaceutical form suitable for its administration by any suitable route. Though virtually any pharmaceutical form can be used, the use of pharmaceutical forms for the parenteral administration of said non-lipidated TF is advantageous.

Therefore, in a particular embodiment, the invention relates to the use of non-lipidated TF, or a non-lipidated fragment thereof, in the preparation of a drug for the parenteral administration of said non-lipidated TF or non-lipidated fragment thereof.

In this case, the pharmaceutical compositions containing non-lipidated TF and pharmaceutically acceptable excipients or carriers, will be adapted for their parenteral administration in the form of, for example, sterile solutions, suspensions or lyophilized products in the suitable dosage form; in this case, said pharmaceutical compositions will include suitable excipients, such as buffers, surfactants, etc. In any case, the excipients will be chosen according to the chosen pharmaceutical administration. Information about said carriers and excipients, as well as about said administration forms suitable for the administration of said product of the invention, can be found in Galenic pharmacy treatises. A review of the different pharmaceutical administration forms of drugs in general, and of their preparation processes, can be found in the book "Tratado de Farmacia Galénica" (*"Galenic Pharmacy Treatise"*), by C. Faulí i Trillo, 1$^{st}$ Edition, 1993, Luzán 5, S. A. of Ediciones.

The dose of non-lipidated TF to be administered to an FVII-deficient subject may vary within a wide range, for example, between about 0.01 µg of active protein/ml and 100 active µg of protein/ml. The non-lipidated TF dose to be administered will depend on several factors, including the characteristics of the TF protein used, such as, for example, its activity and biological half life, TF protein concentration in the formulation, the clinical condition of the patient, the hemorrhagic disorder to be treated, etc.

EXAMPLE

For the purpose of evaluating the capacity of lipidated TF as a stimulator of FXa, a series of in vitro and in vivo assays were performed, specifically:

1. In vitro Assays Demonstrating that Lipidated TF (Alone and Combined) Acts as a Direct Stimulator of FXa Causing Fibrin Clot Formation and Blood Coagulation in the Absence of FVII (Caused by Absence, Deficiency or Immunoblocking)
    1.1 Lipidated TF increases FXa proteolytic activity and accordingly thrombin production in the absence of FVII (chromogenic assays in solution, and in suspension of washed platelets).
    1.2 Lipidated TF is able to coagulate plasma and blood from FVII-deficient patients (coagulation assays in plasma and in non-anticoagulated whole blood).
    1.3 Lipidated TF is able to coagulate plasma healthy subjects in the presence of a monoclonal antibody against FVII (coagulation assays).
    1.4 Combination of lipidated TF and NCIS synergistically increase blood coagulation in FVII deficient plasmas (coagulation assays).
    1.5 Combination of lipidated TF and FXa synergistically increase blood coagulation in the presence of monoclonal antibody against FVII)(coagulation assays in FX deficient plasmas).
    1.6 Combination of lipidated TF, FXa and NCIS synergistically increase coagulation in the presence of antibody anti FVII (coagulation assay in FX deficient plasmas).

2. In vitro Assays Demonstrating that Combination of Lipidated TF with FXa at Low Concentrations (Unable to Induce any Procoagulant Effects), Causes Coagulation of FX Defective Plasmas
    2.1 Lipidated TF acts as a stimulator of FXa when this serine protease in present at low concentrations.
    2.2 Combination of lipidated TF with FXa and NCIS acts synergistically in the stimulation of FXa.

3. in vitro Assays Demonstrating that Lipidated TF (Alone and Combined) Causes Coagulation in Patients with Deficiencies of Other Coagulation Factors Rather than FVH
    3.1 Lipidated TF coagulates plasma and blood from patients with deficiencies in coagulation factors FV, FVIII, FVIII, FIX, FX, FXI, FXII, and FXIII (coagulation assays in coagulation factor-deficient plasmas and in non-coagulated whole blood from FVIII and FIX).
    3.2 Lipidated TF coagulates whole blood and plasma previously heparinized.
    3.3 Lipidated TF coagulates plasma from animals treated with warfarin.
    3.4 Combination of lipidated TF with NCIS synergistically enhance blood coagulation in plasma from patients with deficiencies in coagulation factors FV, FVIII, FVIII, FIX, FX, FXI, FXII, and FXIII (coagulation assays in coagulation factor-deficient plasmas) and in whole blood from hemophilic patients.

4. In vitro Assays Demonstrating that Lipidated TF (Alone and Combined) Causes Blood Coagulation in Healthy Subjects
    4.1 Lipidated TF coagulates plasma and blood from healthy subjects.
    4.2 Combination of lipidated TF with NCIS synergistically enhances blood coagulation in plasma and blood from healthy subjects. Absence of synergic effects when lipidated TF is associated with phospholipids.

5. In vitro Assays Demonstrating the Coagulant Effect of Lipidated TF (Alone and Combined) in Plasma from Patients with Congenital and Acquired (Thrombocytopenic) Platelet Disorders
    5.1 Lipidated TF coagulates plasma from patients with congenital platelet disorders.
    5.2 Combination of lipidated TF with NCIS increase coagulation in whole blood from patients with congenital platelet disorders.
    5.3 Lipidated TF coagulates thrombocytopenic samples.

6. In vivo Assays Demonstrating that TF is an Agent Useful for Topical Antihemorrhagic Treatment in Control Rats (by Applying Directly Alone or in Combination with NCIS on the Blood Vessel Previously Sectioned)
    6.1 Lipidated TF (alone or combined with NCIS) is useful as a topical hemostatic agent in a severe hemorrhage animal model by proximal section of rat tails.
    6.2 Lipidated TF is useful as a topical hemostatic agent in a severe hemorrhage animal model treated previously with heparin or warfarin.
    6.3 Lipidated TF is useful as a topical hemostatic agent in a lethal hemorrhage animal model by proximal section of rat tails.

I. Materials and Methods

Materials

As a source of lipidated TF were used human recombinant Tissue factor (rTF), Thromborel® S, and Neoplastin® Plus. Specifically the following commercial preparations were used: Human Recombinant Tissue Factor (Non-Lipidated) (American Diagnostica, USA), relipidated following the method described by Morrissey; lyofilized human placental thromboplastin containing calcium (Thromborel® S, Dade Behring Inc); lyophilized rabbit brain containing calcium (Neoplastin® Plus, Diagnostica Stago-Roche).

Procoagulant activity of TF protein was determined by a standard curve using as reference material human recombinant lipidated TF (American Diagnostica, USA), and was expressed in the text as µg of active protein/ml and in the tables as µg/ml. For simplicity, in this example, the term rTF or TF refers to lipidated TF unless otherwise stated. Haematologic Technologies commercial compounds were used as sources of FXa, FII, and FVa. Commercial Dade® Actin® FS reagent (Dade Behring) was used as NCIS. Commercial Coagulation Factor deficient plasmas (FV, FVII, FVIII, FIX, FX, FXI, FXII, and FXIII) were purchased from Dade Behring Marburg GmbH.

Methods

Method for Relipidating TF in Lipid Vesicles Using Dialysis with Octylglucoside (Morrisey Method).

Non-lipidated TF is incorporated into lipid vesicles using non ionic detergent N-octyl-beta-D-glucopyranoside (octylglucoside). Both TF and the lipids are dissolved in octylglucoside forming micelles. Octylglucoside can be easily removed from the solution by dialysis due to its high critical micelle concentration (CMC=20 to 50 mM). When the octylglucoside is removed the lipids are organized in unilamellar vesicles. TF is soaked in these vesicles by virtue of its transmembrane domain. Normally, 50 to 80% of TF molecules are arranged facing outwards from the vesicles.

Buffers and Stock Solutions

Octylglucoside (n-octyl-beta-D-glucopyranoside) from Calbiochem.

Lipids:

| Lipid | | Concentration | Molecular weight |
|---|---|---|---|
| PC | L-alpha-phosphatidylcholine | 10 or 25 mg/ml | 761 |
| PS | L-alpha-phosphatidylserine, bovine brain sodium salt | 10 mg/ml | 810 |
| PE | L-alpha-phosphatidylethanolamine, bovine liver | 10 mg/ml | 768 |

Buffers:

HBS 100 mM NaCl
20 mM Hepes/NaOH, pH 7.5
0.02% (m/v) sodium azide

HBSA (keep at 4° C.)

Bovine serum albumin in 0.1% (m/v) HBS

OG/HBS (prepare at time of use)

n-octyl-beta-D-glucopyranoside in 100 mM HBS (29.2 mg OG/ml of HBS)

Preparing the Lipid Solution in Octylglucoside (OG)

1. 2.6 micromols of total lipids are prepared for each sample in a glass tube, using the desired lipid molar radius.
2. Dry the lipid mixture under an argon or nitrogen current.
3. When the tube appears to be dry, vacuum dry another 60 minutes.
4. Add 400 µl of a fresh solution of OG/HBS (at room temperature) to the tube containing the dry lipids.

| For PC:PS vesicles (80:20 molar ratio) | | |
|---|---|---|
| 62 µl PC (at 25 mg/ml) | = 1.58 mg | = 2.08 µmol |
| 42 µl PS (at 10 mg/ml) | = 0.42 mg | = 0.52 µmol |

| For PC:PE:PC vesicles (40:40:20 molar ratio) | | |
|---|---|---|
| 32 µl PC (at 25 mg/ml) | = 0.79 mg | = 1.04 µmol |
| 80 µl PE (at 10 mg/ml) | = 0.80 mg | = 1.04 µmol |
| 42 µl PS (at 10 mg/ml) | = 0.42 mg | = 0.52 µmol |

Relipidating

Add the desired amount of TF to the tube containing the 400 µl of OG/lipids and enough HBSA up to completing the final volume of 1 ml. Carry out this step at room temperature.

Obtaining Washed Platelet Suspensions

Washed platelet suspensions were prepared according to the method described by Radomski M. et al. (Radomski M, Moncada S.; 1983 Thromb Res. This is an improved method for washing of human platelets with prostacyclin. 15;30(4): 383-9) from blood extractions (3.15% sodium citrate) from healthy volunteers. Processing of the specimens was always carried out immediately after blood extraction and at room temperature. Platelet activation and functionality states were assayed by means of aggregation assays prior to and during the performance of the assays. Self-activation and functionality were estimated by means of activation with a known agonist (collagen).

In vitro Assays

Chromogenic Assays

Different chromogenic assays were designed in solution and in activated platelet suspensions to demonstrate the effect of rTF on factor Xa proteolytic activity.

FXa amidolytic activity was determined by means of a chromogenic assay using S-2765 (Chromogenix) as the chromogenic substrate for FXa, whereas thrombin forming activity was analyzed using S-2238 (Chromogenix) as the chromogenic substrate for thrombin.

The chromogenic assays were performed in suspension (in buffer) and using washed platelet suspensions. Suitable volumes of each one of the factors to be studied were dispensed on an ELISA plate and, in the event of using the washed platelet suspension, a suitable volume such as to have a concentration of 250,000 platelets/µl in the medium. Finally, adding the specific chromogenic substrate allowed quantifying the proteolytic activity in question by means of spectrophotometric readings at 405 nm. In the assays for determining amidolytic activity only FXa and the different rTF concentrations were dispensed, whereas in the assays for determining thrombin forming activity it was necessary to further add factor II (prothrombin) and FVa (the latter only in the case of assays in suspension, given that in the washed platelet assays these already contained endogenous FVa).

Coagulation Assays in Plasma

Spontaneous procoagulant activity (unstimulated) in plasma was measured by means of a coagulation assay with a certain step in a coagulometer (Fibrintimer BFT-II clot-timer Dade-Behring, Germany). In short, 50 µl of platelet-poor plasma were added to the already tempered cuvettes and 50 µl of distilled water were added. This mixture was left to incubate for 60 seconds at 37° C. and 50 µl of 25 mM calcium chloride were immediately added and the coagulation time was determined in seconds in the coagulometer, verified by formation of the clot. Each one of the samples was assayed in duplicate. Platelet-poor plasmas were obtained by centrifugation procedure and number of platelets was determined by Coulter.

Coagulation Assays in Whole Blood

Procoagulant activity in non-anticoagulated whole blood was determined by means of a coagulation method. The different agents to be studied were added to 1 ml of non-anticoagulated whole blood and coagulation time was measured with a chronometer from the beginning of the extraction until a stable and consolidated blood clot appeared. The effect of the different agents was evaluated by means of their shortening or lengthening of blood coagulation times.

In vivo Assays

Severe Hemorrhage Model by Rat Tail Proximal Section

23 Sprage-Dawley male rats weighing 350-450 grams were randomly distributed in 3 treatment groups: a control group, made up of 14 animals which received topical treatment with physiological saline solution, whereas the other two groups, also made up of 5 animals, received topical treatment with 1.2 µg/ml rTF, and n=4 topical treatment with 1.2 µg/ml rTF+NCIS (vol:vol 1:2), respectively. All the compounds came into topical contact with the proximal section of the animal's tail to hemostastically act dispensed by a plastic eppendorf pipette. Formation of the stable and consolidated clot was evidenced by means of confumation of no further bleeding.

Severe Hemorrhage Model by Rat Tail Proximal Section in Animals Treated with Anticoagulant Drugs 27 Sprage-Dawley male rats weighing 350-450 grams were randomly distributed in 5 treatment groups: a control group, made up of 14 animals which received topical treatment with physiological saline solution. Two groups received 200 U/Kg of heparin i.v. 15 minutes before to start tail transection procedure (to be treated with TF n=3, and to be treated with Saline n=5), and other two groups received orally 0.1 mg/kg/day of warfarin during three days before to start tail transection procedure(to be treated with TF n=3 and to be treated with saline, n=2). Topical treatment with 1.2 µg/ml rTF was administered to only one of each treatment group. Therefore, it was a control treated group for each anticoagulation treatment. Lipidated TF came into topical contact with the proximal section of the animal's tail to hemostastically act dispensed by a plastic eppendorf pipette. Formation of the stable and consolidated clot was evidenced by means of confirmation of no further bleeding.

Lethal Hemorrhage Model by Puncture in the Carotid Artery of Rats 4 male Sprage-Dawley rats weighing 350-450 grams were randomly distributed in 2 treatment groups each including 2 animals. The control group animals received physiological saline solution as treatment, whereas the other group received lipidated TF administered topically (at the final dose of 2 µg of active protein). Lethal hemorrhage model by puncture in the carotid artery of rats was carried out following standard procedures. Lipidated TF and the physiological saline solution were administered directly on the point of the puncture in a dressing containing 3 ml of each. This was combined with the pressure and contact of the corresponding treatment during two minutes.

II. Results

1. In vitro Assays Demonstrating that Lipidated TF (Alone and Combined) Acts as a Direct Stimulator of FXa Causing Fibrin Clot Formation and Blood Coagulation in the Absence of FVII (Caused by Absence, Deficiency or Immunoblocking)

1.1. Lipidated TF Increases FXa Proteolytic Activity and Accordingly Thrombin Production in the Absence of FVII Several in vitro assays were performed for the purpose of evaluating lipidated TF capacity as a factor Xa stimulating agent in the absence of FVII: (i) chromogenic assays for FXa amidolytic activity in solution; and (ii) chromogenic assays for thrombin forming activity in washed platelet suspension.

Chromogenic Assays for FXa Amidolytic Activity

Direct assays for FXa amidolytic activity in solution using FXa-specific substrate S-2765, demonstrated that lipidated TF is able to very significantly increase FXa proteolytic activity. In the presence of high rTF concentrations (1 µg/ml) an increase of activity produced by low and high FXa concentrations ($p<0.001$) was observed. Similar significant stimulating effects ($p<0.001$) were observed in the presence of lower lipidated TF concentrations (0.1 µg/ml). Table 1 shows the results obtained in 5 independent experiments.

TABLE 1

Lipidated TF, in the absence of FVII, increases FXa proteolytic activity in the absence of FVII

|  | Without rTF | rTF 0.1 µg/ml | rTF 1 µg/ml |
| --- | --- | --- | --- |
| FXa 30 nM | 550 ± 51 | 2,108 ± 61 | 3,316 ± 89 |
| FXa 5 nM | 0 | 341 ± 32 | 505 ± 63 |

Mean ± SEM (n = 5)

Chromogenic Assays for Thrombin Forming Activity in Washed Platelet Suspensions

The procoagulant effect detected was much greater when platelet suspensions were used as the source of the procoagulant surface and thrombin formation was determined by means of specific substrate S-2238 (table 2). In the absence of exogenous FXa, lipidated TF produced a significant stimulating effect on thrombin formation ($p<0.001$). Similar stimulating effects were observed in the presence of exogenous FXa both at low and high concentrations ($p<0.001$).

TABLE 2

Lipidated TF induces thrombin formation in washed platelets in the presence of FII but in the absence of FVa (already present in platelets) and FVII

|  | Without rTF | rTF 0.1 µg/ml | rTF 1 µg/ml |
| --- | --- | --- | --- |
| FXa 1,250 pM | 421 ± 19 | 13,854 ± 145 | 14,910 ± 168 |
| FXa 250 pM | 213 ± 21 | 9,324 ± 155 | 9,610 ± 114 |
| FXa 125 pM | 201 ± 29 | 7,802 ± 113 | 8,508 ± 178 |
| FXa absent | 0 | 906 ± 89 | 3,504 ± 69 |

Mean ± SEM (n = 5)

1.2. Lipidated TF is Able to Coagulate Plasma and Blood from FVII-Deficient Patients (Coagulation Assays in Plasma and in Non-Anticoagulated Whole Blood)

A series of in vitro coagulation assays were performed showing the coagulating effect of lipidated TF in plasma and non-anticoagulated whole blood from FVII-deficient patients and, therefore, lipidated TF is a useful agent for antihemorrhagic treatment.

Coagulation Assays in Commercially FVII Depleted Plasma and Non-Anticoagulated Whole Blood from FVII Deficient Patients The effect of lipidated TF on coagulation was investigated by means of coagulation assays using commercially FVII depleted plasma and non-anticoagulated whole blood from 2 patients with FVII-deficiency (table 3). Lipidated TF in a concentration-dependent manner was able to significantly accelerate coagulation in defective FVII plasmas. In the same way, non-anticoagulated whole blood from FVII-deficient patients were also coagulated in the presence of low, medium and high lipidated TF concentrations, indicating that it is able to produce normal coagulation by lipidated TF even in the absence of FVII. Table 3 shows the results obtained from 5 independent experiments for depleted FVII plasmas.

TABLE 3

Demonstration of the procoagulant effect of lipidated TF in FVII-deficient plasmas

| | Coagulation time (s) | | | |
|---|---|---|---|---|
| | | With rTF | | |
| | Basal | 1 µg/ml | 0.1 µg/ml | 0.01 µg/ml |
| Normal plasma | 215.1 ± 24.6 | 11.1 ± 0.2 | 15.3 ± 0.2 | 25.7 ± 0.4 |
| FVII-deficient plasma | >300 | 67.7 ± 7.2 | 113.7 ± 28.3 | 202.7 ± 41.6 |

Mean ± SEM (n = 5)

The effect of lipidated TF on blood from healthy volunteer was significant after the concentration of 0.01 µg/ml, whereas greater concentrations were necessary in FVII-deficient patients (table 4). Although significant procoagulant effects (p<0.00 1) being detected after 0.1 µg/ml, lipidated TF was able to normalize coagulation time at the concentration of 0.01 µg/ml, there being no differences between coagulation times detected in normal subjects at basal conditions and in FVII-deficient subjects with said lipidated TF concentration. Finally, although lipidated TF at 1 µg/ml was not able to induce the same strong procoagulant effect in FVII depleted plasma a very significant effect was observed, which indicates that lipidated TF can normalize hemostasis in these patients.

TABLE 4

Procoagulant effect of lipidated TF in non-anticoagulated whole blood from healthy and FVII-deficient individuals

| | rTF | | | | | |
|---|---|---|---|---|---|---|
| | Basal | 0.01 ng/ml | 0.1 ng/ml | 1 ng/ml | 10 ng/ml | 100 ng/ml |
| Control sample no. 1 | 5.8 | 4.7 | 4.4 | 3.3 | 2.1 | 1.3 |
| Control sample no. 2 | 7.2 | 6.7 | 5.5 | 3.7 | 2.1 | 1.0 |
| Patient no. 6 FVII-deficient | 11.4 | n.d. | 10.5 | 9.5 | 5.2 | 2.3 |
| Patient no. 7 FVII-deficient | 12.5 | n.d | 11.3 | 10.5 | 6.3 | 3.1 | n.d.; not determined

1.3. Lipidated TF is Able to Coagulate Plasma Healthy Subjects in the Presence of a Monoclonal Antibody Against FVII (Coagulation Assays)

In vitro coagulation assays were performed showing the coagulating effect of lipidated TF in plasma in healthy subjects in the presence of a monoclonal antibody against FVII (this antibody is able to block coagulation in normal plasmas).

Coagulation Assays in Normal Plasma Depleted of FVII by Blocking with Anti FVII

The effect of lipidated TF on plasma coagulation was investigated by means of coagulation assays using plasmas from healthy volunteers in the presence of a monoclonal antibody against FVII (table 5). Lipidated TF was able to cause coagulation even in the presence of a monoclonal antibody against FVII, (which is able to inhibit completely blood coagulation). Under these experimental conditions (like FVII-deficient samples), lipidated TF is able to produce plasma coagulation.

TABLE 5

Demonstration of the procoagulant effect of TF in normal plasma in the presence of a monoclonal antibody against FVII

| | Without rTF | With rTF 1 µg/ml |
|---|---|---|
| Normal plasma | 126.8 | 28.1 |
| Normal plasma with anti FVII (400 µg/ml) | 216.8 | 42.5 |

1.4. Combination of Lipidated TF and NCIS Synergistically Increase Blood Coagulation in FVII Deficient Plasmas (Coagulation Assays)

A series of in vitro coagulation assays were performed showing the coagulant effect of lipidated TF associated with negatively charged inorganic surfaces [NCIS] in FVII defective plasma. Said procoagulant effect exceeded the one obtained when lipidated TF was used alone as a procoagulant agent. These results show that the effect mediated by lipidated TF is independent of FVII and is able to induce plasma coagulation even in the absence of its specific ligand. Table 6 shows the results obtained in 5 independent experiments.

TABLE 6

Procoagulant effect of rTF associated with negatively charged inorganic surfaces in heparinized and coagulation factor-deficient plasmas

| | Coagulation time (s) | | |
|---|---|---|---|
| | Basal | With rTF | |
| | — | 1 µg/ml | 1 µg/ml + NCIS |
| Normal plasma | 211.1 ± 18.5 | 18.6 ± 0.1 | 13 ± 1.2* |
| FVII deficient plasma | >300 | 67 ± 11 | 32 ± 3.4* |

Mean ± SEM (n = 5);
*p < 0.001 without NCIS vs. with NCIS; t-Student 1.5. Combination of Lipidated TF and FXa Synergistically Increase Blood Coagulation in the Presence of Monoclonal Antibody against FVII (Coagulation Assays in FX Deficient Plasmas)

The procoagulant effects of the association of lipidated TF and FXa at low concentrations (170 pM and 1700 pM) in the absence of FVII were investigated in FXa deficient-plasma immunoblocked with anti FVII (Table 7).

TABLE 7

Procoagulant effect of lipidated TF associated with FXa in FXa deficient-plasma in the absence of FVII (immunoblocked with anti FVII)

| | Coagulation time (s) | | |
|---|---|---|---|
| FXa deficient-plasma | Without FXa | With FXa (1700 pM) | With FXa (170 pM) |
| Basal (5 mM calcium) | >400 | 133 ± 18 | 290 ± 10.2 |
| Plus rTF 1 µg/ml | 253.5 ± 11 | 83.1 ± 3.2* | 124 ± 6.1* |
| Plus rTF 1 µg/ml + anti FVII (400 µg/ml) | 234.5 ± 9 | 78 ± 2* | 124 ± 6.1* |

Mean ± SEM (n = 5);
*p < 0.001 without FXa vs. FXa. t-Student 1.6. Combination of Lipidated TF, FXa and NCIS Synergistically Increase Blood Coagulation in the Presence of Monoclonal Antibody Against FVII (Coagulation Assays in FX Deficient Plasmas)

The procoagulant effects of the association of lipidated TF, FXa at low concentrations (170 pM and 1700 pM) and NCIS were also were investigated in FXa deficient-plasma (Table 8).

TABLE 8

Procoagulant effect of rTF associated with FXa and NCIS in FXa deficient-plasma

| | Coagulation time (s) | | |
|---|---|---|---|
| FXa deficient-plasma | | With NCIS (1 µl) | With NCIS (2 µl) |
| Basal (5 mM calcium) | >400 | >400 | 290 ± 10.2 |
| rTF 1 µg/ml + FXa (170 pM) | 124 ± 6.1* | 109 ± 4.1* | 84 ± 3* |
| rTF 1 µg/ml + FXa (1700 pM) | 83.1 ± 3.2* | 65.5 ± 5.2* | 45.5 ± 3.2* |
| rTF 1 µg/ml + FXa (170 pM) + anti FVII (400 µg/ml) | 119 ± 5* | 101 ± 5* | 99 ± 3* |
| rTF 1 µg/ml + FXa (1700 pM) + anti FVII (400 µg/ml) | 78 ± 2 | 27.7 ± 1.2 | 25 ± 2 |

Mean ± SEM (n = 5);
*p < 0.001 without NCIS vs. NCIS. t-Student

2. In vitro Assays Demonstrating that Combination of Lipidated TF with FXa at Low Concentrations (Unable to Induce any Procoagulant Effects), Causes Coagulation of FX Defective Plasmas 2.1. Lipidated TF Acts as a Stimulator of FXa when this Serine Protease in Present at Low Concentrations In vitro coagulation assays were performed in coagulation FX deficient plasma to show the synergistic effect of lipidated TF on FXa (added at low concentrations, 170 pM and 1700 pM, to FX deficient plasma, therefore these plasmas are unable to produce FXa from any coagulation pathway). The procoagulant effects of the association of lipidated TF and FXa at low concentrations are shown in Table 9.

TABLE 9

Procoagulant effect of lipidated TF associated with FXa in FXa deficient-plasma

| | Coagulation time (s) | | |
|---|---|---|---|
| FX deficient-plasma | Without FXa | With FXa (1700 pM) | With FXa (170 pM) |
| Basal (5 mM calcium) | >400 | 133 ± 18 | 290 ± 10.2 |
| Plus rTF 1 µg/ml | 253.5 ± 11 | 83.1 ± 3.2* | 124 ± 6.1* |

Mean ± SEM (n = 5);
*p < 0.001 without FXa vs. FXa. t-Student 2.2. Combination of Lipidated TF with FXa and NCIS Acts Synergistically in the Stimulation of FXa The procoagulant effects of the association of lipidated TF, FXa at low concentrations (170 pM and 1700 pM) and NCIS were also were investigated in FX deficient-plasma (Table 10).

TABLE 10

Procoagulant effect of lipidated TF associated with FXa and NCIS in FX deficient-plasma

| | Coagulation time (s) | | |
|---|---|---|---|
| FX deficient-plasma | | With NCIS (1 µl) | With NCIS (2 µl) |
| Basal (5 mM calcium) | >400 | >400 | 290 ± 10.2 |
| rTF 1 µg/ml + FXa (170 pM) | 124 ± 6.1* | 109 ± 4.1* | 84 ± 3* |
| rTF 1 µg/ml + FXa (1700 pM) | 83.1 ± 3.2* | 65.5 ± 5.2* | 45.5 ± 3.2* |

Mean ± SEM (n = 5);
*p < 0.001 without NCIS vs. NCIS; t-Student

3. In vitro Assays Demonstrating that Lipidated TF (Alone and Combined) Causes Blood Coagulation in Patients with Deficiencies in Other Coagulation Factors Rather than FVII 3.1. Lipidated TF Coagulates Plasma and Blood from Patients with Deficiencies in Coagulation Factors FV, FVIII, FVIII, FIX, FX, FXI, FXII, and FXIII The procoagulant effect of lipidated TF (alone) on coagulation factor-deficient plasmas was investigated using commercial plasmas depleted by means of immunoaffinity techniques, as well as plasma from 3 patients diagnosed with hemophilia A (FVIII-deficient) and 2 diagnosed with hemophilia B (FIX-deficient). Table 11 shows the results. At the concentration of 1 µg/ml lipidated TF was able to effectively coagulate all the plasmas with deficiencies in FV, FVIII, FIX, FX, FXI, FXII and FXIII. On the other hand, in the absence of the known FXa cofactor, FVa, lipidated TF was also able to produce plasma coagulation, although only at high and medium concentrations. In the remaining coagulation factor deficiencies, lipidated TF was effective at all the concentrations used, with excellent results being obtained at very low concentrations. Even in the absence of FX (1%) lipidated TF was able to coagulate but only at high concentrations. All these results were confirmed with samples from patients with hemophilia A and hemophilia B.

TABLE 11

Procoagulant effect of lipidated TF in coagulation factor-deficient plasmas

| | Coagulation time (s) | | | |
|---|---|---|---|---|
| | Without rTF | With rTF | | |
| | — | 1 µg/ml | 0.1 µg/ml | 0.01 µg/ml |
| Normal plasma | 215.1 ± 24.6 | 11.1 ± 0.2 | 15.3 ± 0.2 | 25.7 ± 0.4 |
| FV-D plasma | >600 | 84.3 ± 15.2 | 123.3 ± 24.5 | 350 ± 29.5 |
| FVIII-D plasma | >600 | 15.5 ± 2.3 | 21.5 ± 2.8 | 32.1 ± 2.6 |
| FIX-D plasma | >600 | 14.8 ± 3.2 | 22.3 ± 2.5 | 34.6 ± 2.4 |
| FX-D plasma | >600 | 446.2 ± 32 | >600 | >600 |
| FXI-D plasma | >600 | 14.3 ± 0.5 | 19.4 ± 1.5 | 27.3 ± 0.6 |
| FXII-D plasma | >600 | 16.2 ± 0.3 | 22.5 ± 1.1 | 32.5 ± 0.5 |
| FXIII-D plasma | >600 | 14.2 ± 0.3 | 21.5 ± 1.0 | 30.5 ± 0.5 |
| Hemophilia A plasma | >600 | 12.2 ± 1.5 | 13.8 ± 0.6 | 21.3 ± 0.8 |
| Hemophilia B plasma | >600 | 12.1 ± 0.5 | 15.3 ± 0.4 | 26.8 ± 0.6 |

Mean ± SEM (n = 5)

The procoagulant effect of lipidated TF (alone) in human non-anticoagulated whole blood from people suffering from hemophilia A and B, was evaluated by means of a coagulation assay. Clot formation was determined by estimating the time in minutes for the clot to consolidate. The effect of lipidated TF in blood from healthy volunteers was significant from concentrations of 0.001 µg/ml, whereas greater doses were required in hemophilic patients, significant procoagulant effects (p<0.001) being detected from 0.01 µg/ml. At the concentration of 0.1 µg/ml lipidated TF was able to completely normalize coagulation time, there being no differences between the coagulation times detected in normal subjects and hemophilic subjects. Table 12 shows the results obtained from 4 samples from healthy individuals (sample numbers 1-4), 3 from patients suffering hemophilia A and 2 with hemophilia B.

TABLE 12

Procoagulant effect of lipidated TF in non-anticoagulated whole blood from healthy subjects and Hemophilic patients

| | | rTF | | |
|---|---|---|---|---|
| | Basal | 0.001 µg/ml | 0.01 µg/ml | 0.1 µg/ml |
| Sample control no. 1 | 5.8 | 3.3 | 2.1 | 1.3 |
| Sample control no. 2 | 7.2 | 3.7 | 2.1 | 1.0 |
| Sample control no. 3 | 7.2 | 4.2 | 2.1 | 0.9 |
| Sample control no. 4 | 7.5 | 3.8 | 2.0 | 1.0 |
| Patient no. 1 Hemophilia A | 13.3 | 8.0 | 4.6 | 1.6 |
| Patient no. 2 Hemophilia A | 17.3 | 9.0 | 5.6 | 1.0 |
| Patient no. 3 Hemophilia A | 15.3 | 12.4 | 7.0 | 1.5 |
| Patient no. 4 Hemophilia B | 20.5 | 11.1 | 6.1 | 1.5 |
| Patient no. 5 Hemophilia B | 16.3 | 11.3 | 5.5 | 1.6 |

Coagulation time (expressed in minutes): the time the clot takes to consolidate in a non-anticoagulated blood sample 3.2. Lipidated TF Coagulates Whole Blood and Plasma Previously Heparinized Lipidated TF was able to coagulate plasmas (table 13) and whole non anticoagulated blood (table 14) previously incubated with high heparin concentrations, demonstrating that its effect on FXa is independent of the inhibitory effect mediated by this anticoagulant drug and, even in the presence of heparin-type inhibitors

TABLE 13

Effect of lipidated TF on heparinized plasma (coagulation time in seconds)

| | Without lipidated TF | With lipidated TF |
|---|---|---|
| Control | 320.4 ± 160 | 17.2 ± 1 |
| Heparin 3 U/ml | >600 | 58 ± 12 |

TABLE 14

Effect of lipidated TF on heparinized whole blood (coagulation time in min)

| | Without lipidated TF | With lipidated TF |
|---|---|---|
| Control | 3.96 ± 0.54 | 0.4 ± 0.28 |
| Heparin 0.25 U/ml | 12.45 ± 0.69 | 15.7 ± 0.22 |
| Heparin 1 U/ml | 26.6 ± 5.76 | 4.5 ± 2.38 |

3.3. Lipidated TF Coagulates Plasma from Animals Treated with Warfarin

Lipidated TF was able to coagulate plasmas from warfarin treated rats following the procedure detailed in the methods. The results show in the table 15 indicate that even when the synthesis of all vitamin K-dependent coagulation factors are abolished, lipidated TF is able to coagulate, demonstrating that its effect on FXa is independent of the inhibitory effect mediated by this anticoagulant drugs.

TABLE 15

Effect of lipidated TF on plasma from warfarin-treated animals (coagulation time in seconds)

| | Without lipidated TF | With lipidated TF (1 µg/ml) |
|---|---|---|
| Control | 49 ± 10.2 | 10.9 ± 2.2 |
| Warfarin-treated plasmas (0.1 mg/kg for 3 days) | 60.1 ± 5.6 | 12.8 ± 3.2 |

3.4. Combination of Lipidated TF with NCIS Synergistically Enhance Blood Coagulation in Plasma from Patients with Deficiencies in Coagulation Factors FV, FVII, FVIII, FIX, FX, FXI, FXII, and FXIII (Coagulation Assays in Coagulation Factor-Deficient Plasmas) and in Whole Blood from Hemophilic Patients A series of in vitro coagulation assays were performed showing the coagulant effect of lipidated TF associated with NCIS in plasma from coagulation factor-deficient patients (FV, FVII, FVIII, FIX, FX, FXI, FXII, and FXIII). Said procoagulant effect exceeded the one obtained when lipidated TF was used alone as a procoagulant agent. Even at low concentrations (1 µg/ml) with which lipidated TF was not able to coagulate the FV-deficient plasma (FV-D plasma), the combination of both agents produced a significant procoagulant effect. Likewise, similar synergistic effects were obtained when FVII-deficient plasma (FVII-D plasma) was used. These results show that the effect mediated by lipidated TF is independent of FVII and is able to induce plasma coagulation even in the absence of FV. Similarly, the combination (lipidated TF+NCIS) also exerted potent procoagulant effects in plasma samples from hemophilic patients (A and B). Table 16 shows the results obtained in 5 independent experiments.

TABLE 16

Procoagulant effect of rTF associated with NCIS in coagulation factor-deficient plasmas

| | Coagulation time (s) | | |
|---|---|---|---|
| | Without rTF | With rTF | |
| | — | 1 µg/ml | 1 µg/ml + NCIS |
| Normal plasma | 281.1 ± 12.5 | 11.1 ± 0.2 | 9.1 ± 0.4* |
| FV-D plasma | >600 | 84.3 ± 15.2 | 55.2 ± 2.3* |
| FVIII-D plasma | >600 | 15.5 ± 2.3 | 10.1 ± 0.5* |
| FIX-D plasma | >600 | 14.8 ± 3.2 | 10.3 ± 0.2* |
| FX-D plasma | >600 | 446.2 ± 32 | 253.5 ± 19* |
| FXI-D plasma | >600 | 14.3 ± 0.5 | 11.5 ± 0.6* |
| FXII-D plasma | >600 | 16.2 ± 0.3 | 12.9 ± 1.5* |
| FXIII-D plasma | >600 | 14.2 ± 0.3 | 10.8 ± 0.9* |
| Hemophilia A plasma | >600 | 12.2 ± 1.5 | 10.4 ± 0.9* |
| Hemophilia B plasma | >600 | 12.1 ± 0.5 | 10.1 ± 0.8* |

Mean ± SEM (n = 5);
*$p < 0.001$ without NCIS vs. with NCIS; t-Student

The procoagulant effect in non-anticoagulated whole blood of lipidated TF and NCIS combination was also investigated by means of coagulation assays using blood from patients suffering hemophilia A (3 patients) and B (2 patients). By comparison with the assays in which lipidated TF was alone (table 12), the procoagulant effect of the association (rTF+NCIS) was significantly ($p<0.001$) greater (table 17).

TABLE 17

Procoagulant effect of rTF together with NCIS in whole blood

| | Without NCIS | With NCIS |
|---|---|---|
| Sample control | 7.1 ± 0.6 | 6.0 ± 1.4* |
| rTF 0.1 µg/ml | 1.1 ± 0.9 | 0.5 ± 0.1* |
| | Basal | rTF 0.1 µg/ml + NCIS |
| Patient no. 1 Hemophilia A | 13.3 | 6.8* |
| Patient no. 2 Hemophilia A | 17.3 | 7.2* |
| Patient no. 3 Hemophilia A | 15.3 | 9.1* |

TABLE 17-continued

Procoagulant effect of rTF together with NCIS in whole blood

| Patient no. 4 Hemophilia B | 20.5 | 8.5* |
| Patient no. 5 Hemophilia B | 16.3 | 8.6* |

Coagulation time (expressed in minutes): the time the clot takes to consolidate in a non-anticoagulated blood sample

4. In vitro Assays Demonstrating that Lipidated TF (Alone and Combined) Causes Blood Coagulation in Healthy Subjects

4.1. Lipidated TF Coagulates Plasma and Blood from Healthy Subjects

A series of in vitro coagulation assays were performed showing the coagulant effect of lipidated TF in plasma and non anticoagulated whole blood from healthy volunteers without histories of hemostasic disorders. Table 18 shows the results obtained from 5 independent experiments in healthy plasmas and table 19 in non anticoagulated whole blood.

TABLE 18

Procoagulant effect of lipidated TF in plasma from healthy subjects

| Normal plasma | Coagulation time (s) |
|---|---|
| Basal | 281.08 ± 12.5 |
| rTF 0.0001 µg/ml | 201 ± 12.2 |
| rTF 0.0001 µg/ml | 184 ± 5.8 |
| rTF 0.01 µg/ml | 73.5 ± 2.3 |
| rTF 0.1 µg/ml | 28.6 ± 0.1 |
| rTF 1 µg/ml | 16.4 ± 0.9 |

Mean ± SEM (n = 5)
non-lipidated TF at the same concentrations was unable to modify coagulation time

TABLE 19

Procoagulant effect of TF in non anticoagulated blood from healthy subjects

| | | rTF | | |
|---|---|---|---|---|
| | Basal | 0.01 µg/ml | 0.1 µg/ml | 1 µg/ml |
| Sample no. 1 | 5.8 | 3.3 | 2.1 | 1.3 |
| Sample no. 2 | 7.2 | 3.7 | 2.1 | 1.0 |
| Sample no. 3 | 7.2 | 4.2 | 2.1 | 0.9 |
| Sample no. 4 | 7.5 | 3.8 | 2.0 | 1.0 |

4.2. Combination of Lipidated TF with NCIS Synergistically Enhances Blood Coagulation in Plasma and Blood from Healthy Subjects. Absence of Synergic Effects when Lipidated TF is Associated with Phospholipids A series of in vitro coagulation assays were performed showing the coagulant effect of rTF associated with NCIS in plasma from healthy volunteers. Table 20 shows the results obtained from 5 independent experiments. By comparison with the assays in which rTF was alone, the procoagulant effect of the association (rTF+NCIS) was significantly ($p<0.001$) greater in each and every one of the concentrations used.

TABLE 20

Procoagulant effect of lipidated TF associated with NCIS in normal plasma

| Normal plasma | Coagulation time (s) | |
|---|---|---|
| | Without NCIS | With NCIS |
| Basal | 281.08 ± 12.5 | 167 ± 10* |
| rTF 0.0001 µg/ml | 201 ± 12.2 | 69 ± 0.8* |
| rTF 0.001 µg/ml | 184 ± 5.8 | 44.9 ± 3.2* |
| rTF 0.01 µg/ml | 73.5 ± 2.3 | 30.6 ± 2.5* |
| rTF 0.1 µg/ml | 28.6 ± 0.1 | 16 ± 4.2* |
| rTF 1 µg/ml | 16.4 ± 0.9 | 12.8 ± 0.5* |

Mean ± SEM (n = 5);
*p < 0.001 without NCIS vs. with NCIS; t-Student

Table 21 shows the absence of synergic effects when lipidated TF is associated with phospholipids. (0.66 mM of PC/PS; phosphatydilcholine/phosphatydilserine at different molar ratio).

TABLE 21

Effect of phospholipids on lipidated TF procoagulant activity

| Lipidated TF (0.1 µg/ml) | Coagulation time (s) |
|---|---|
| Without PC/PS | 37.9 |
| With PC/PS 90/10 | 44 |
| 80/20 | 39.7 |
| 70/30 | 41.7 |
| 60/40 | 40.1 |
| 50/50 | 43.5 |
| 40/60 | 34.6 |
| 30/70 | 41.5 |
| 20/80 | 44.3 |
| 10/90 | 41.9 |

5. In vitro Assays Demonstrating the Coagulant Effect of Lipidated TF (Alone and Combined) in Blood from Patients with Congenital and Acquired (Thrombocytopenic) Platelet Disorders.

5.1. Lipidated TF Coagulates Whole Blood from Patients with Congenital Platelet Disorders The procoagulant effect of lipidated TF on blood coagulation in patients with platelet disorders was investigated by means of coagulation assays using blood from 2 patients suffering Glanzmann's disease and Bernard Soulier syndrome. rTF was able to very significantly accelerate, and in a concentration-dependent manner, blood coagulation in individuals suffering from Glannmann's disease and Bernard Soulier syndrome (Table 22); rTF is therefore a useful agent for the antihemorragic treatment of said individuals.

TABLE 22

Procoagulant effect of TF in patients with platelet disorders

| | | rTF | | |
|---|---|---|---|---|
| | Basal | 0.01 µg/ml | 0.1 µg/ml | 1 µg/ml |
| Sample control no. 1 | 5.8 | 3.3 | 2.1 | 1.3 |
| Patient no. 6 Glanzmann's dis. | 13.6 | 7.3 | 3.4 | 2.9 |
| Patient no. 7 Bernard-Soulier S. | 11.9 | 7.1 | 4.1 | 3.1 |

5.2. Combination of Lipidated TF with NCIS Increases Coagulation in Whole Blood from Patients with Congenital Platelet Disorders A series of in vitro coagulation assays were performed showing the coagulant effect of rTF associated with NCIS in whole blood from patients with congenital platelet disorders. Table 23 shows the results obtained from two patients with Glanzmann's disease and Bernard-Soulier Syndrome. By comparison with the assays in which rTF was alone, the procoagulant effect of the association (rTF+NCIS) was significantly (p<0.001) greater in each patient.

TABLE 23

Procoagulant effect of rTF together with NCIS in whole blood

| | Without NCIS | With NCIS |
|---|---|---|
| Sample control | 7.1 ± 0.6 | 6.0 ± 1.4* |
| rTF 0.1 µg/ml | 1.1 ± 0.9 | 0.5 ± 0.1* |

| | Basal | rTF 0.1 µg/ml + NCIS |
|---|---|---|
| Patient no. 6 Glanzmann's dis. | 13.6 | 4.7* |
| Patient no. 7 Bernard-Soulier S. | 11.9 | 4.6* |

Coagulation time (expressed in minutes): the time the clot takes to consolidate in a non-anticoagulated blood sample.
*p < 0.001 without NCIS vs. NCIS. t-Student 5.3. Lipidated TF Coagulates Thrombocytopenic Samples A series of in vitro coagulation assays were performed showing the coagulant effect of lipidated TF in plasmas with different platelet count. Table 24 shows the results obtained from normal platelet count to thrombocytopenic conditions.

TABLE 24

Effect of lipidated TF on thrombocytopenic samples

| Platelet count | Without lipidated TF | With lipidated TF (1 µg/ml) |
|---|---|---|
| 350,000/µl | 226.3 | 21.9 |
| 150,000/µl | 232.6 | 22.8 |
| 50,000/µl | 253.9 | 22.4 |
| 9,000/µl | 321.2 | 21.3 |
| <1,000/µl | >400 | 21.3 |

6. In vivo Assays Demonstrating that TF is an Agent Useful for Topical Antihemorrhagic Treatment in Control Rats (by Applying Directly on the Blood Vessel Previously Sectioned)

6.1. Lipidated TF is Useful as a Topical Hemostatic Agent in a Severe Hemorrhage Animal Model by Proximal Section of Rat Tails In vivo assays were performed showing that lipidated TF administered alone or associated with NCIS is a useful agent for topical antihemorragic treatment. The use of lipidated TF as a topical hemostatic agent administered alone or combined NCIS was evaluated by means of the use of a severe hemorrhage in an animal model by proximal section of rat tails. The results obtained are shown in Table 25. As can be seen, in said severe hemorrhage model, the hemorrhage spontaneously coagulated in the control animals (PSS Control, treated with physiological saline solution) at 18.1±5.98 minutes; however, topical administration of lipidated rTF (alone) produced a significant reduction (11.1±5.54 minutes, p<0.001). When rTF was administered in combination with NCIS the procoagulant effect was even greater (5.0±1.1 minutes; p<0.001).

TABLE 25

Severe hemorrhage model by proximal section of rat tails. Bleeding coagulation time

| | Bleeding coagulation time |
|---|---|
| Control Saline group (n = 14) | 18.16 ± 5.98 |
| Lipidated TF treated group (n = 5) | 11.1 ± 5.5 |
| Lipidated TF + NCIS (n = 4) | 5.0 ± 1.1 |

The results are expressed as the time in minutes to reach consolidated coagulation., Under the same experimental conditions non-lipidated TF (n=3) was evaluated. No effects were observed and bleeding coagulation time was similar to the control animals. These results indicate that non-lipidated TF was not useful to treat topically bleeding episodes.

6.2. Lipidated TF is Useful as a Topical Hemostatic Agent in a Severe Hemorrhage Animal Model Treated Previously with Heparin or Warfarin In vivo assays were performed showing that lipidated TF administered alone is a useful agent for topical antihemorragic treatment in anticoagulant conditions (table 25). The use of lipidated TF as a topical hemostatic agent administered alone was evaluated by means of the use of a severe hemorrhage in an animal model by proximal section of rat tails treated previously with 200 U/Kg of heparin i.v. 15 minutes before to start tail transection procedure, or with orally 0.1 mg/kg/day of warfarin during three days before to start tail transection procedure. The results obtained are shown in Table 26. As can be seen, in said severe hemorrhage model, the control saline group, treated with physiological saline solution, spontaneously coagulated at 18.1±5.98 minutes. Control heparin-treated group hemorrhage did not spontaneously coagulate (>90 minutes). Control warfarin-treated group spontaneously coagulated at 41.6±8.5 minutes. Table 26 shows that topical administration of lipidated TF (alone) produced a significant reduction in all treatment groups.

TABLE 26

Severe hemorrhage model by proximal section of rat tails in anticoagulated treated animals. Bleeding coagulation time

| | Bleeding coagulation time (min) |
|---|---|
| Control Saline group (n = 14) | 18.16 ± 5.98 |
| Control heparin-treated group (n = 5) | >90 |
| Control warfarin-treated group (n = 2) | 41.6 ± 8.5 |
| Heparin-treated group (n = 3) + lipidated TF | 26.3 ± 2.5 |
| Warfarin-treated group (n = 3) + lipidated TF | 4.5 ± 2.5 |

The results are expressed as the time in minutes to reach consolidated coagulation 6.3. Lipidated TF is Useful as a Topical Hemostatic Agent in a Lethal Hemorrhage Animal Model by Puncture in Carotid Artery In vivo assays were performed showing that rTF administered alone is a useful agent for topical antihemorrhagic treatment directly applied on the blood vessel. The use of rTF administered alone was evaluated by means of the use of a lethal hemorrhage in an animal model by puncture in the carotid artery. The results obtained are shown in Table 27 and were very significant. As can be seen, in the group of control animals, (PSS Control, treated with physiological saline solution), all the animals died from bleeding, whereas in the group of lipidated TF no animal died and the section could be successfully sealed and coagulated in all cases. The treatment was effective in terms of the time necessary to achieve the stable coagulation and sealing of the puncture wound.

TABLE 27

Lethal hemorrhage model by puncture in carotid artery of rats

| | Control SF | | rTF |
|---|---|---|---|
| animal no. 1 | Death | animal no. 3 | 125 |
| animal no. 2 | Death | animal no. 4 | 135 |
| Mean ± SD | | | 130 ± 7.1 |

The results are expressed as the time in seconds to reach consolidated coagulation and sealing of the puncture wound. rTF administered as is indicated in the text at the dose of 2 µg of acive protein).

In Conclusion:

Results from Example Number 1 Clearly Demonstrate that:
1) In the absence of its ligand, FVII, lipidated TF is able to interact directly with FXa significantly increasing its proteolytic activity (both amidolytic and thrombin forming), this results show for the first time a new role for lipidated TF, acting as a new cofactor for FXa (independent of the well known FVa).
2) Lipidated TF is able to coagulate FVII defective plasmas. Therefore, lipidated TF is a good alternative for the treatment of these patients (at the present the unique treatment is the expensive human recombinant FVIIa).
3) Lipidated TF acts synergistically with NCIS and FXa (at low concentrations unable to produce coagulation).

Results from Example Number 2 Clearly Demonstrate that:
1) Lipidated TF causes that physiological FXa concentrations, unable to produce any significant procoagulant effect, trigger prothrombin hydrolysis and consequently thrombin formation takes place.
2) Lipidated TF has a new role acting as a cofactor for all proteolytic activities of all forms of FXa (soluble and bound to prothrombinase complex).
3) Even FX defective plasmas (containing traces of FX) may be coagulated by lipidated TF. Therefore, lipidated TF is a good alternative for the treatment of these patients.
4) Lipidated TF acts synergistically with NCIS in the stimulation effect of FXa activity.

Results from Example Number 3 Clearly Demonstrate that:
1) Lipidated TF is able to cause blood coagulation in Hemophilic patients (FVIII, FIX and FXI). Therefore, lipidated TF is a good alternative for the treatment of these patients.
2) Lipidated TF is able to cause blood coagulation even in the absence of FV. These results clearly show that lipidated TF causes a strong stimulatory effect on FXa, because in the absence of its cofactor (deficient FV plasmas), lipidated TF acts as cofactor causing the same stimulatory effect.
3) Lipidated TF is able to cause blood coagulation even in the FX defective plasmas (containing traces of FX). Therefore, lipidated TF is an alternative for the treatment of these patients.
4) Lipidated TF is able to cause blood coagulation in heparin and warfarin treated plasmas, indicating, that lipidated TF interferes in the effect of antithrombin III and probably through its stimulatory effect on FXa basal concentrations may coagulate even in warfarin treated conditions.

5) Finally, lipidated TF acts synergistically with NCIS in the procoagulant effect observed in all factor coagulation deficiencies.

Results from Example Number 4 Clearly Demonstrate that:
1) Lipidated TF is able to cause blood coagulation in Healthy subjects. Therefore, lipidated TF is a good alternative for the treatment of bleeding episodes in healthy subjects.
2) Lipidated TF acts synergistically with NCIS but not with only phospholipids in the procoagulant effect observed in healthy subjects.

Results from Example Number 5 Clearly Demonstrate that:
1) Lipidated TF is able to cause blood coagulation in patients with platelet disorders, such as congenital and acquired (i.e. thrombocytopenia). Therefore, lipidated TF is a good alternative for the treatment of bleeding episodes in patients with alterations of platelet number and/or functionality.

Results from Example Number 6 Clearly Demonstrate that:
1) Lipidated TF topically administered is able to stop bleeding in an animal model of severe hemorrhage (proximal total tail transection).
2) Lipidated TF topically administered is able to stop bleeding in an animal model of severe hemorrhage (proximal total tail transection) complicated with anticoagulant therapy (heparin or warfarin).
3) Lipidated TF topically administered is able to stop bleeding in an animal model of lethal hemorrhage (carotid puncture in carotid artery).

The invention claimed is:

1. A method of treating hemorrhages in a subject in need thereof, said method comprising administering an effective blood coagulating amount of a medicament to the subject, said medicament comprising lipidated Tissue Factor (TF), or a functional fragment thereof, wherein said functional fragment is capable of binding to the FXa, wherein said subject is a healthy subject or a subject with a hemorrhagic diathesis, where said hemorrhagic diathesis comprises a coagulopathy and/or a platelet disorder, and wherein the medicament is topically administered to the subject.

2. The method according to claim 1, wherein said coagulopathy is a congenital coagulopathy or an acquired coagulopathy.

3. The method according to claim 2, wherein said congenital coagulopathy is a coagulopathy based on a deficiency of a coagulation factor selected from the group consisting of coagulation Factor V, coagulation Factor VII, coagulation Factor VIII, coagulation Factor IX, coagulation Factor X, coagulation Factor XI, coagulation Factor XII, coagulation Factor XIII and combinations thereof.

4. The method according to claim 2, wherein said subject has an acquired coagulopathy produced by an anticoagulant treatment with anticoagulants.

5. The method according to claim 4, wherein the anticoagulants are selected from the group consisting of heparin, low molecular weight heparins, warfarin, coumarin derivatives and dicoumarins.

6. The method according to claim 1, wherein said subject has a congenital or acquired platelet disorder.

7. The method according to claim 6, wherein said congenital platelet disorder is selected from the group consisting of Glanzmann's disease, Bernard Soulier syndrome, Bolin-Jamieson's syndrome, Wiskott-Aldrich syndrome, Paris-Trousseau-Jacobsen syndrome, thrombocytopenia of the X chromosome, the Gray platelet syndrome, Sebastian syndrome and Fanconi anemia.

8. The method according to claim 6, wherein said acquired platelet disorder is selected from the group consisting of thrombocytemia, polycytemia, chronic myelocytic leukemia, myeloid metaplasia, disproteinemias in scurvy, in congenital heart disease, and in cirrhosis.

9. The method according to claim 1, wherein said lipidated TF is lipidated human TF.

10. The method of claim 1, further comprising administering an effective amount of activated coagulation Factor X (FXa), wherein the administration of the FXa and medicament comprising TF is sequential.

11. The method of claim 10, wherein the FXa is topically administered to the subject.

12. The method of claim 1, further comprising administering an effective amount of negatively charged inorganic surface (NCIS), wherein said NCIS comprises a mixture of lipids with anionic character and one or more blood coagulation accelerators selected from the group consisting of ellagic acid, zeolite, silica and inorganic oxide materials, wherein the mixture of lipids include neutral or zwitterionic lipids and/or negatively charged lipids, wherein the administration of the NCIS and medicament comprising TF is sequential.

13. The method of claim 12, wherein the NCIS is topically administered to the subject.

14. The method of claim 1, wherein the medicament further comprises FXa for simultaneous administration of TF and FXa.

15. The method of claim 1, wherein the medicament further comprises NCIS for simultaneous administration of TF and NCIS, wherein said NCIS comprises a mixture of lipids with anionic character and one or more blood coagulation accelerators selected from the group consisting of ellagic acid, zeolite, silica and inorganic oxide materials, wherein the mixture of lipids include neutral or zwitterionic lipids and/or negatively charged lipids.

16. The method of claim 14, wherein the medicament further comprises NCIS for simultaneous administration of TF, FXa and NCIS, wherein said NCIS comprises a mixture of lipids with anionic character and one or more blood coagulation accelerators selected from the group consisting of ellagic acid, zeolite, silica and inorganic oxide materials, wherein the mixture of lipids include neutral or zwitterionic lipids and/or negatively charged lipids.

17. A method of treating hemorrhages in a subject in need thereof, said method comprising administering an effective blood coagulating amount of a medicament to the subject, said medicament comprising lipidated Tissue Factor (TF), wherein said subject is a healthy subject or a subject with a hemorrhagic diathesis, where said hemorrhagic diathesis comprises a coagulopathy and/or a platelet disorder, and wherein the medicament is topically administered to the subject.

* * * * *